(12) United States Patent
Stein

(10) Patent No.: US 11,690,730 B2
(45) Date of Patent: Jul. 4, 2023

(54) LORDOTIC EXPANDABLE FUSION IMPLANT

(71) Applicant: NuVasive, Inc., San Diego, CA (US)

(72) Inventor: Christopher Stein, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 178 days.

(21) Appl. No.: 17/201,218

(22) Filed: Mar. 15, 2021

(65) Prior Publication Data

US 2021/0267767 A1 Sep. 2, 2021

Related U.S. Application Data

(63) Continuation of application No. 16/068,606, filed as application No. PCT/US2016/069453 on Dec. 30, 2016, now Pat. No. 10,973,650.

(60) Provisional application No. 62/273,441, filed on Dec. 31, 2015, provisional application No. 62/273,390, filed on Dec. 30, 2015.

(51) Int. Cl.
*A61F 2/44* (2006.01)
*A61F 2/46* (2006.01)
*A61F 2/30* (2006.01)

(52) U.S. Cl.
CPC .......... *A61F 2/4455* (2013.01); *A61F 2/4611* (2013.01); *A61F 2002/30538* (2013.01); *A61F 2002/30556* (2013.01); *A61F 2002/30827* (2013.01)

(58) Field of Classification Search
CPC combination set(s) only.
See application file for complete search history.

(56) References Cited

U.S. PATENT DOCUMENTS

| 5,171,278 | A | 12/1992 | Pisharodi |
|---|---|---|---|
| 5,390,683 | A | 2/1995 | Pisharodi |
| 5,693,100 | A | 12/1997 | Pisharodi |
| 5,725,588 | A | 3/1998 | Errico |
| 5,782,832 | A | 7/1998 | Larsen et al. |
| 6,102,950 | A | 8/2000 | Vaccaro |
| 6,126,689 | A | 10/2000 | Brett |
| 6,174,334 | B1 | 1/2001 | Suddaby |
| 6,183,517 | B1 | 2/2001 | Suddaby |
| 6,332,895 | B1 | 12/2001 | Suddaby |
| 6,340,369 | B1 | 1/2002 | Ferree |
| 6,344,058 | B1 | 2/2002 | Ferree |
| 6,352,557 | B1 | 3/2002 | Ferree |
| 6,368,351 | B1 | 4/2002 | Glenn et al. |
| 6,409,766 | B1 | 6/2002 | Brett |

(Continued)

FOREIGN PATENT DOCUMENTS

| AU | 2007202404 | 6/2007 |
|---|---|---|
| AU | 2011203582 | 8/2011 |

(Continued)

OTHER PUBLICATIONS

International Search Report for application No. PCT/US2016/069453, ISA/EP, dated Apr. 6, 2017, 3 pgs.

(Continued)

*Primary Examiner* — Sameh R Boles
(74) *Attorney, Agent, or Firm* — Hoffman Warnick LLC

(57) ABSTRACT

The present disclosure provides an expandable spinal implant comprising a plurality of moveable endplates pivotably connect to a housing.

20 Claims, 28 Drawing Sheets

(56) References Cited

U.S. PATENT DOCUMENTS

| | | |
|---|---|---|
| 6,419,702 B1 | 7/2002 | Ferree |
| 6,488,710 B2 | 12/2002 | Besselink |
| 6,491,724 B1 | 12/2002 | Ferree |
| 6,500,205 B1 | 12/2002 | Michelson |
| 6,582,451 B1 | 6/2003 | Marucci et al. |
| 6,648,918 B2 | 11/2003 | Ferree |
| 6,652,584 B2 | 11/2003 | Michelson |
| 6,709,458 B2 | 3/2004 | Michelson |
| 6,716,247 B2 | 4/2004 | Michelson |
| 6,719,797 B1 | 4/2004 | Ferree |
| 6,743,255 B2 | 6/2004 | Ferree |
| 6,793,679 B2 | 9/2004 | Michelson |
| 6,808,537 B2 | 10/2004 | Michelson |
| 6,814,756 B1 | 11/2004 | Michelson |
| 6,962,606 B2 | 11/2005 | Michelson |
| 6,972,035 B2 | 12/2005 | Michelson |
| 6,986,772 B2 | 1/2006 | Michelson |
| 7,008,453 B1 | 3/2006 | Michelson |
| 7,044,971 B2 | 5/2006 | Suddaby |
| 7,070,598 B2 | 7/2006 | Lim et al. |
| 7,083,650 B2 | 8/2006 | Moskowitz et al. |
| 7,087,055 B2 | 8/2006 | Lim et al. |
| 7,118,579 B2 | 10/2006 | Michelson |
| 7,118,598 B2 | 10/2006 | Michelson |
| 7,547,325 B2 | 6/2009 | Biedermann et al. |
| 7,608,107 B2 | 10/2009 | Michelson |
| 7,615,052 B2 | 11/2009 | Serbousek |
| 7,621,951 B2 | 11/2009 | Glenn et al. |
| 7,625,377 B2 | 12/2009 | Veldhuizen et al. |
| 7,655,027 B2 | 2/2010 | Michelson |
| 7,678,148 B2 | 3/2010 | Peterman |
| 7,682,400 B2 | 3/2010 | Zwirkoski |
| 7,763,028 B2 | 7/2010 | Lim et al. |
| 7,763,074 B2 | 7/2010 | Altarac et al. |
| 7,846,206 B2 | 12/2010 | Oglaza et al. |
| 7,892,286 B2 | 2/2011 | Michelson |
| 7,901,409 B2 | 3/2011 | Canaveral et al. |
| 7,922,729 B2 | 4/2011 | Michelson |
| 8,007,534 B2 | 8/2011 | Michelson |
| 8,025,665 B2 | 9/2011 | Lim et al. |
| 8,075,621 B2 | 12/2011 | Michelson |
| 8,097,034 B2 | 1/2012 | Michelson |
| 8,097,035 B2 | 1/2012 | Glenn et al. |
| 8,128,662 B2 | 3/2012 | Altarac et al. |
| 8,152,837 B2 | 4/2012 | Altarac et al. |
| 8,182,538 B2 | 5/2012 | O'Neil et al. |
| 8,251,891 B2 | 8/2012 | Moskowitz et al. |
| 8,268,001 B2 | 9/2012 | Butler et al. |
| 8,303,658 B2 | 11/2012 | Peterman |
| 8,317,798 B2 | 11/2012 | Lim et al. |
| 8,328,818 B1 | 12/2012 | Seifert et al. |
| 8,377,071 B2 | 2/2013 | Lim et al. |
| 8,409,282 B2 | 4/2013 | Kim |
| 8,444,692 B2 | 5/2013 | Michelson |
| 8,496,664 B2 | 7/2013 | Michelson |
| 8,523,944 B2 | 9/2013 | Jimenez et al. |
| 8,540,452 B2 | 9/2013 | Jimenez et al. |
| 8,551,173 B2 | 10/2013 | Lechmann et al. |
| 8,579,907 B2 | 11/2013 | Lim et al. |
| 8,603,173 B2 | 12/2013 | Biedermann et al. |
| 8,628,577 B1 | 1/2014 | Jimenez |
| 8,663,329 B2 | 3/2014 | Ernst |
| 8,685,095 B2 | 4/2014 | Miller et al. |
| 8,690,917 B2 | 4/2014 | Suh et al. |
| 8,828,085 B1 | 4/2014 | Jensen |
| 8,734,520 B2 | 5/2014 | Zwirkoski |
| 8,771,321 B2 | 7/2014 | Michelson |
| 8,771,358 B2 | 7/2014 | Michelson |
| 8,795,365 B2 | 8/2014 | Arcenio et al. |
| 8,795,374 B2 | 8/2014 | Chee |
| 8,845,726 B2 | 9/2014 | Tebbe et al. |
| 8,845,730 B2 | 9/2014 | De Villiers et al. |
| 8,894,652 B2 | 11/2014 | Seifert et al. |
| 8,906,100 B2 | 12/2014 | Jimenez et al. |
| 8,940,049 B1 | 1/2015 | Jimenez et al. |
| 8,986,386 B2 | 3/2015 | Oglaza et al. |
| 8,998,992 B2 | 4/2015 | Seifert et al. |
| 9,005,291 B2 | 4/2015 | Loebl et al. |
| 9,034,040 B2 | 5/2015 | Seifert et al. |
| 9,039,742 B2 | 5/2015 | Altarac et al. |
| 9,119,726 B2 | 9/2015 | Wei |
| 9,125,692 B2 | 9/2015 | Kim |
| 9,138,327 B1 | 9/2015 | McClellan, III |
| 9,155,572 B2 | 10/2015 | Altarac et al. |
| 9,204,973 B2 | 12/2015 | Aflatoon et al. |
| 9,220,535 B2 | 12/2015 | Robling et al. |
| 9,233,009 B2 | 1/2016 | Gray et al. |
| 9,259,328 B2 | 2/2016 | Pabst et al. |
| 9,289,308 B2 | 3/2016 | Marino et al. |
| 9,295,562 B2 | 3/2016 | Lechmann et al. |
| 9,333,093 B2 | 5/2016 | Aflatoon |
| 9,345,584 B2 | 5/2016 | Michelson |
| 9,351,846 B2 | 5/2016 | De Villiers et al. |
| 9,351,851 B2 | 5/2016 | Huffmaster et al. |
| 9,381,092 B2 | 7/2016 | Jimenez et al. |
| 9,393,130 B2 | 7/2016 | Suddaby et al. |
| 9,408,707 B2 | 8/2016 | Oglaza et al. |
| 9,408,721 B2 | 8/2016 | Eastlack et al. |
| 9,414,933 B2 | 8/2016 | Banouskou |
| 9,421,111 B2 | 8/2016 | Baynham |
| 9,433,510 B2 | 9/2016 | Lechmann et al. |
| 9,445,856 B2 | 9/2016 | Seifert et al. |
| 9,445,917 B2 | 9/2016 | Jimenez et al. |
| 9,463,099 B2 | 10/2016 | Levy et al. |
| 9,801,734 B1 * | 10/2017 | Stein ............... A61F 2/447 |
| 2003/0236520 A1 | 12/2003 | Lim et al. |
| 2005/0080422 A1 | 4/2005 | Otte et al. |
| 2005/0278036 A1 | 12/2005 | Leonard et al. |
| 2006/0004455 A1 | 1/2006 | Leonard et al. |
| 2007/0118222 A1 | 5/2007 | Lang |
| 2007/0149978 A1 | 6/2007 | Shezifi et al. |
| 2007/0282443 A1 | 12/2007 | Globerman et al. |
| 2008/0114367 A1 | 5/2008 | Meyer |
| 2009/0076607 A1 | 3/2009 | Aalsma et al. |
| 2009/0157084 A1 | 6/2009 | Aalsma et al. |
| 2009/0281628 A1 | 11/2009 | Oglaza et al. |
| 2010/0137862 A1 | 6/2010 | Diao et al. |
| 2010/0137987 A1 | 6/2010 | Diao et al. |
| 2010/0217335 A1 | 8/2010 | Chirico et al. |
| 2011/0029086 A1 | 2/2011 | Glazer et al. |
| 2011/0093074 A1 | 4/2011 | Glerum |
| 2011/0257748 A1 | 10/2011 | Liu |
| 2012/0101530 A1 | 4/2012 | Robling et al. |
| 2012/0185049 A1 | 7/2012 | Varela |
| 2012/0290094 A1 | 11/2012 | Lim et al. |
| 2013/0103154 A1 | 4/2013 | Trieu et al. |
| 2013/0116791 A1 | 5/2013 | Theofilos |
| 2013/0144388 A1 | 6/2013 | Emery et al. |
| 2013/0190876 A1 | 7/2013 | Drochner et al. |
| 2013/0297029 A1 | 11/2013 | Kana et al. |
| 2013/0304213 A1 | 11/2013 | Aflatoon et al. |
| 2014/0018922 A1 | 1/2014 | Marino et al. |
| 2014/0031940 A1 | 1/2014 | Banouskou |
| 2014/0039625 A1 | 2/2014 | To et al. |
| 2014/0114420 A1 | 4/2014 | Robinson |
| 2014/0135776 A1 | 5/2014 | Huffmaster et al. |
| 2014/0148904 A1 | 5/2014 | Robinson |
| 2014/0156007 A1 | 6/2014 | Pabst et al. |
| 2014/0163682 A1 | 6/2014 | Iott et al. |
| 2014/0163683 A1 | 6/2014 | Seifert et al. |
| 2014/0180419 A1 | 6/2014 | Dmuschewsky |
| 2014/0236296 A1 | 8/2014 | Wagner et al. |
| 2014/0243983 A1 | 8/2014 | Galea et al. |
| 2014/0277139 A1 | 9/2014 | Vrionis et al. |
| 2014/0277471 A1 | 9/2014 | Gray |
| 2014/0277492 A1 | 9/2014 | Wei |
| 2014/0277498 A1 | 9/2014 | Ainsworth et al. |
| 2014/0277499 A1 | 9/2014 | Ainsworth et al. |
| 2014/0277508 A1 | 9/2014 | Baynham |
| 2014/0277510 A1 | 9/2014 | Robinson |
| 2014/0296984 A1 | 10/2014 | Etminan |
| 2014/0309741 A1 | 10/2014 | Ganter et al. |
| 2014/0343677 A1 | 11/2014 | Davis et al. |
| 2014/0343678 A1 | 11/2014 | Suddaby et al. |

(56) References Cited

U.S. PATENT DOCUMENTS

| | | |
|---|---|---|
| 2014/0358246 A1 | 12/2014 | Levy et al. |
| 2014/0364951 A1 | 12/2014 | De Villiers et al. |
| 2015/0012097 A1 | 1/2015 | Ibarra |
| 2015/0012098 A1 | 1/2015 | Eastlack et al. |
| 2015/0112437 A1 | 4/2015 | Davis et al. |
| 2015/0173917 A1 | 6/2015 | Radcliffe |
| 2015/0182347 A1 | 7/2015 | Robinson |
| 2015/0230935 A1 | 8/2015 | Aflatoon |
| 2015/0238230 A1 | 8/2015 | Suh et al. |
| 2015/0272743 A1 | 10/2015 | Jimenez et al. |
| 2015/0342586 A1 | 12/2015 | Lim et al. |
| 2016/0022434 A1 | 1/2016 | Robinson |
| 2016/0022438 A1 | 1/2016 | Lamborne et al. |
| 2016/0030190 A1 | 2/2016 | Robinson |
| 2016/0067056 A1 | 3/2016 | Armstrong et al. |
| 2016/0074174 A1 | 3/2016 | Halverson et al. |
| 2016/0081724 A1 | 3/2016 | Robling et al. |
| 2016/0089247 A1 | 3/2016 | Nichols et al. |
| 2016/0242927 A1 | 8/2016 | Seifert et al. |
| 2016/0250034 A1 | 9/2016 | Loebl et al. |
| 2016/0256148 A1 | 9/2016 | Huffmaster et al. |

FOREIGN PATENT DOCUMENTS

| | | |
|---|---|---|
| CN | 101502436 | 8/2009 |
| CN | 202568534 | 12/2012 |
| CN | 203183090 | 9/2013 |
| CN | 104248465 | 12/2014 |
| CN | 204306881 | 5/2015 |
| CN | 105232191 | 1/2016 |
| CN | 204931904 | 1/2016 |
| DE | 20314708 | 11/2003 |
| DE | 10344019 | 5/2005 |
| EP | 2777633 | 9/2014 |
| FR | 2717068 | 9/1995 |
| FR | 2813519 | 3/2002 |
| FR | 3006169 | 12/2014 |
| JP | 2008054710 | 3/2008 |
| JP | 2011516181 A | 5/2011 |
| JP | 2011520580 A | 7/2011 |
| JP | 2013508031 A | 3/2013 |
| JP | 2014073405 | 4/2014 |
| JP | 2015533337 A | 11/2015 |
| JP | 2016013460 | 1/2016 |
| KR | 20020084349 | 11/2002 |
| RU | 2070006 | 12/1996 |
| WO | 1992014423 A1 | 9/1992 |
| WO | 1995025485 | 9/1995 |
| WO | 2001003616 | 1/2001 |
| WO | 2005006944 | 1/2005 |
| WO | 2006042334 | 4/2006 |
| WO | 2007038349 | 4/2007 |
| WO | 2007070024 | 6/2007 |
| WO | 2008003952 A1 | 1/2008 |
| WO | 2008044057 | 4/2008 |
| WO | 2010078468 | 7/2010 |
| WO | 2012089317 | 7/2012 |
| WO | 2014091028 | 6/2014 |
| WO | 2014144696 | 9/2014 |
| WO | 2014186384 | 11/2014 |
| WO | 2015063719 | 5/2015 |
| WO | 2015063721 | 5/2015 |
| WO | 2015097416 | 12/2015 |
| WO | 2015198335 | 12/2015 |
| WO | 2016040125 | 3/2016 |

OTHER PUBLICATIONS

Written Opinion of the International Searching Authority for application No. PCT/US2016/069453, ISA/EP, dated Apr. 6, 2017, 5 pgs.

\* cited by examiner

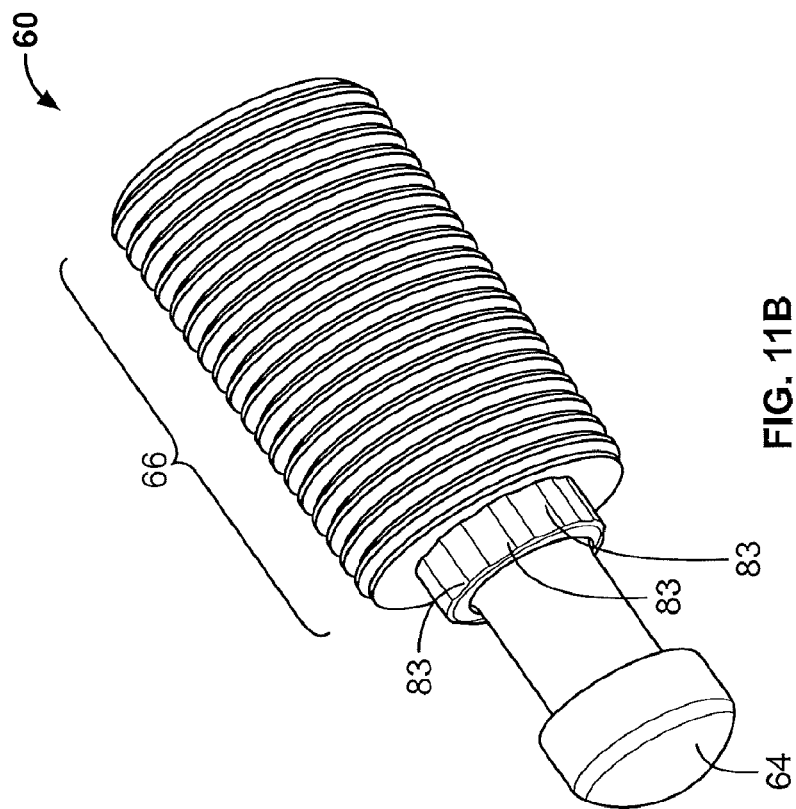
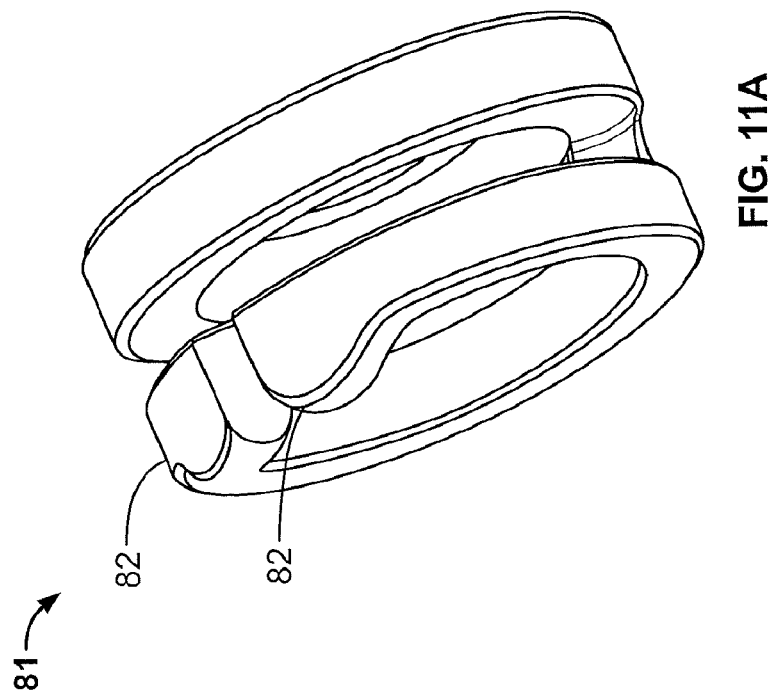
FIG. 11A
FIG. 11B

LORDOTIC EXPANDABLE FUSION IMPLANT

CROSS REFERENCE TO OTHER APPLICATIONS

This application claims priority to, and the benefit of, United States Provisional Patent Application Nos.: 62/273,390 filed Dec. 30, 2015 and 62/273,441 filed Dec. 31, 2015.

FIELD OF THE DISCLOSURE AND BACKGROUND

The present disclosure pertains to the field spinal implants. More specifically, the present disclosure relates to an expandable spinal fusion implant for use in spine surgery, an insertion tool for use with the expandable fusion implant and a measurement tool useful during spinal surgery.

The expandable spinal fusion implant may be used in combination with bone graft materials to facilitate fusion across the intervertebral region.

BRIEF DESCRIPTION OF THE DRAWINGS

To further illustrate the advantages and features of the present disclosure, a more particular description of the invention will be rendered by reference to specific embodiments which are illustrated in the drawings. It is appreciated that these drawings are not to be considered limiting in scope. The invention will be described and explained with additional specificity and detail through the use of the accompanying drawings in which:

FIG. 11A shows one embodiment of the locking collar of the present disclosure.

FIG. 11B shows one embodiment of the lead screw of the present disclosure.

FIG. 18 shows a side view of the expandable spinal implant of the present disclosure in the expanded configuration.

SUMMARY OF THE DISCLOSURE

Figure 1:
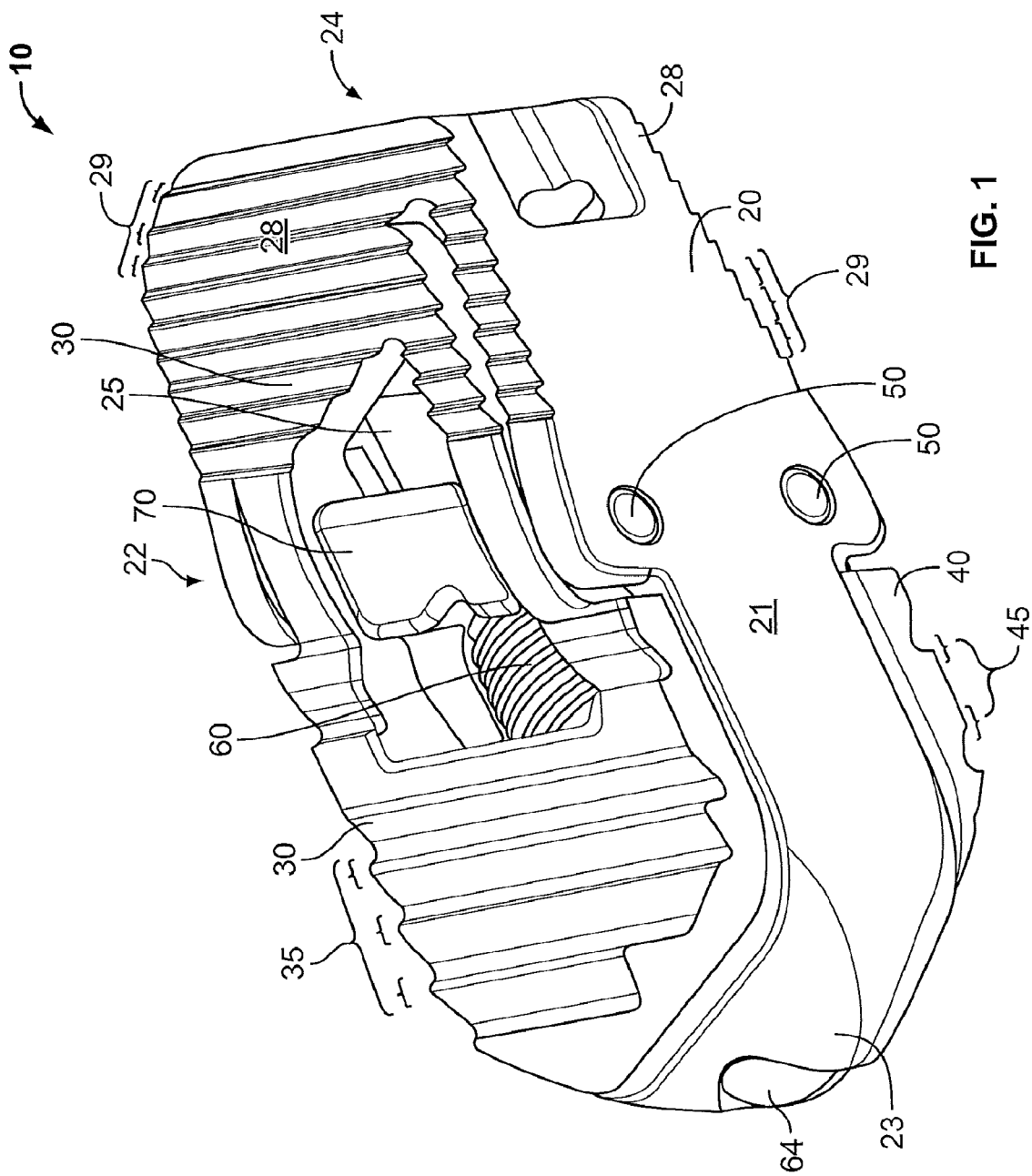
FIG. 1 shows one embodiment of the expandable spinal implant disclosed herein.

In a first aspect, the present disclosure provides an expandable spinal implant comprising a plurality of moveable endplates pivotably connect to a housing. In a second aspect, the present disclosure provides an expandable spinal implant comprising a plurality of moveable endplates pivotably connect to a housing, a central body, a lead screw engaged with the central body and a passive locking mechanism.

DETAILED DESCRIPTION

Unless otherwise defined, all terms used herein have the same meaning as commonly understood by one of ordinary skill in the art of this disclosure. It will be further understood that terms, such as those defined in commonly used dictionaries, should be interpreted as having a meaning that is consistent with their meaning in this context of the specification and should not be interpreted in an idealized or overly formal sense unless expressly so defined herein. Well known functions or constructions may not be described in detail herein for brevity or clarity.

The terminology used herein is for the purpose of describing particular embodiments only and is not intended to be limiting. As used herein, the singular foil is "a", "an" and "the" are intended to include the plural forms as well, unless the context clearly indicates otherwise.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. Numerical quantities given herein are approximate unless stated otherwise, meaning that the term "about" or "approximately" can be inferred when not expressly stated.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The expandable spinal fusion implant and related instruments disclosed herein boast a variety of novel features and components that warrant patent protection, both individually and in combination.

In general, the implant 10 described herein includes a housing 20, upper and lower moveable endplates 30, 40, a central body 70 positioned between the upper and lower endplates 30, 40 and within the housing 20, and a lead screw 60. The implant 10 is designed to be inserted into the disc space between adjacent vertebral bodies. The implant 10 may be made of any suitable, biocompatible material or combination of materials. For example, the implant components may be metal, poly ether ether ketone (PEEK), or a combination of the metal and PEEK. The implant 10 is configured to be inserted into the disc space in a collapsed state and upon being seated in a desired location within the disc space the distal end of the implant is expanded in height to create an implant 10 with a lordotic angle (i.e. the anterior height of the implant 10 is greater than the posterior height of the implant 10, thereby restoring a more natural lordotic curvature of the particular segment of the lumbar spine).

Now, referring to FIGS. 1-19, various embodiments of the implant 10 and its features and elements are shown. The implant 10 includes a housing 20 and upper and lower moveable endplates 30, 40 which are pivotably connected to the housing 20 via pins 50. The upper and lower moveable endplates 30, 40 are pivoted about the housing 20 by the action of a lead screw 60 coupled to a central body 70 as described herein.

Figure 2:
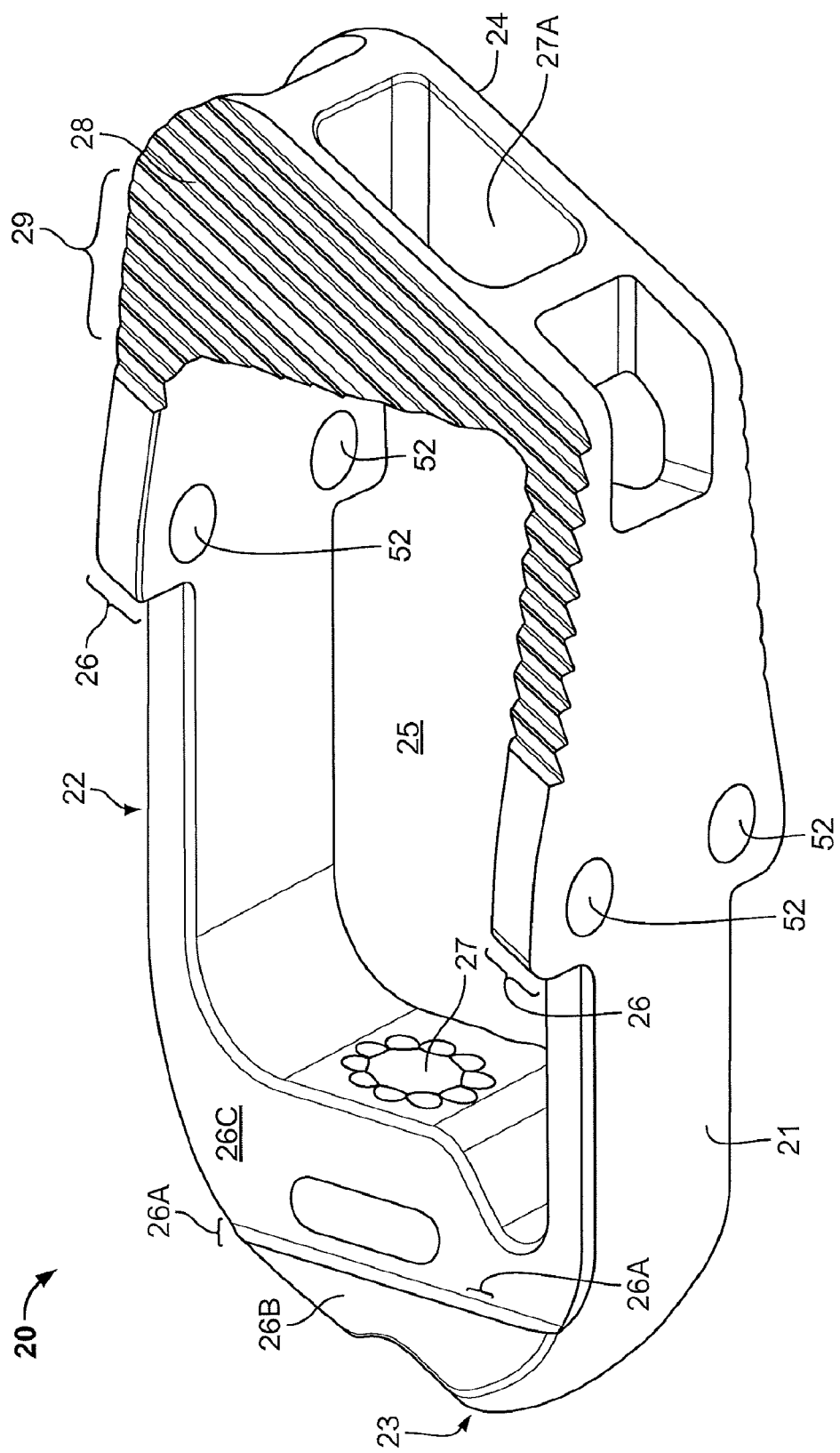
FIG. 2 shows one embodiment of the housing of the expandable spinal implant disclosed 3 herein.

The housing 20 is comprised of first and second lateral walls 21, 22 which are opposite one another and separated by a first and second end wall 23, 24 which are likewise opposite of one another. The first and second lateral walls 21, 22 and first and second end walls 23, 24 define a hollow or empty space which both serves to enclose the various elements required for expanding the implant 10 (as discussed in more detail below) and a fusion aperture 25. The housing may be shaped in a variety of shapes such as a parallelogram as depicted in the FIGS. 4B and C, of course rectangular and square configurations of the housing 20 should be considered within the scope of this disclosure. The first end wall 23 may be tapered to aid insertion into the disc space as shown in FIGS. 1 and 2. The first wall 23 also may include an aperture 27 which receives the rounded end 64 of the drive screw 60 to help secure the drive screw 60 in position. Further, the second end wall 24 comprises an aperture 27A through bone graft composition material can be passed into the fusion aperture 25 after the implant 10 is inserted.

The housing 20 may also have one or more fixed horizontal or nearly horizontal sections 28 that contact the vertebral bodies adjacent the disc space in which the implant 10 is inserted. The fixed horizontal section 28 may have anti-migration features 29 which help prevent shifting of the implant 10 insertion. The anti-migration features 29 may be teeth as depicted herein and may also be treated (for example, through a sandblasting like procedure) to produce a coarse or rough surface on the anti-migration features 29 to encourage bone growth.

Figure 3:
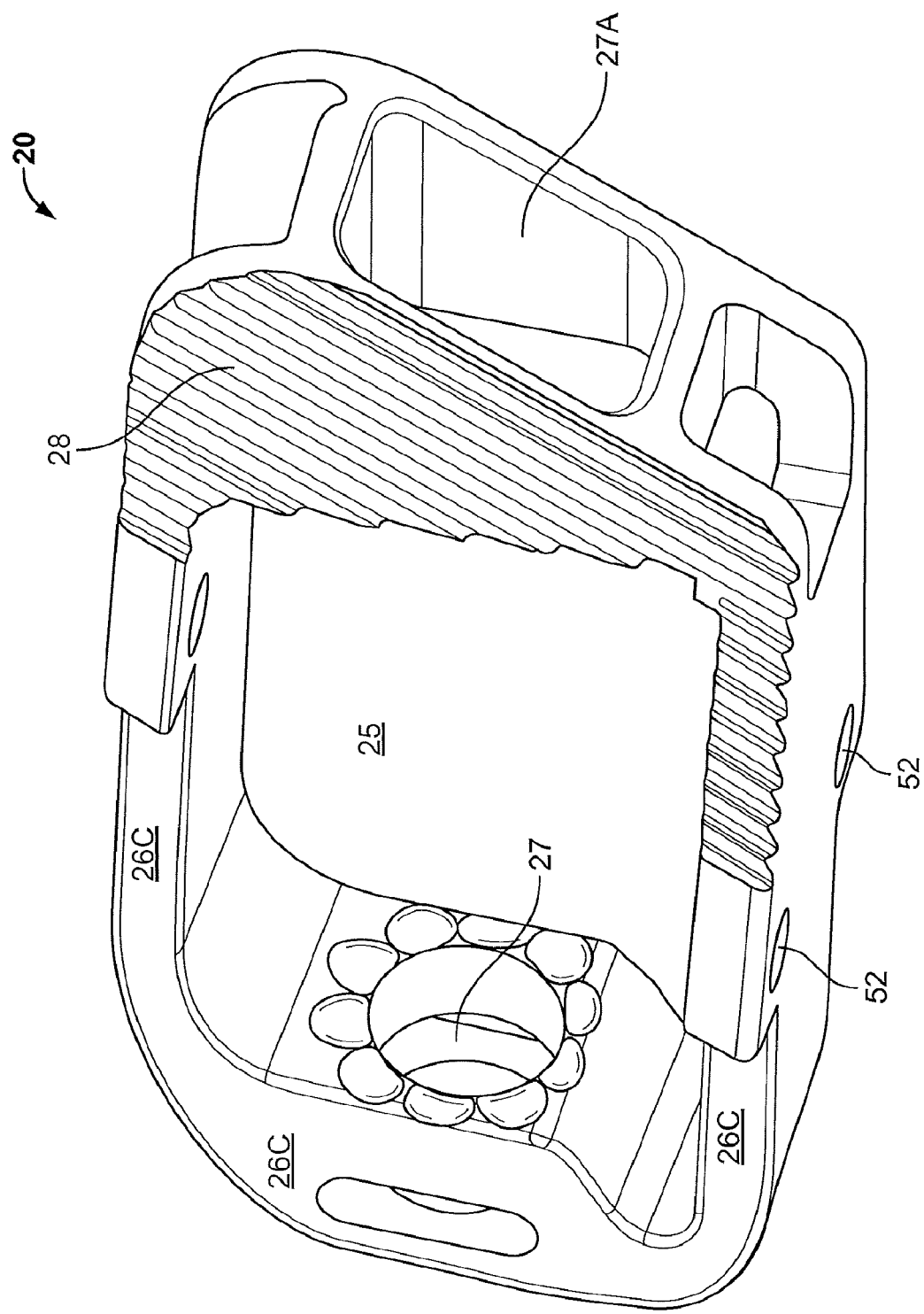
FIG. 3 shows an alternate embodiment of the housing of the expandable spinal implant disclosed herein.
Figure 4:
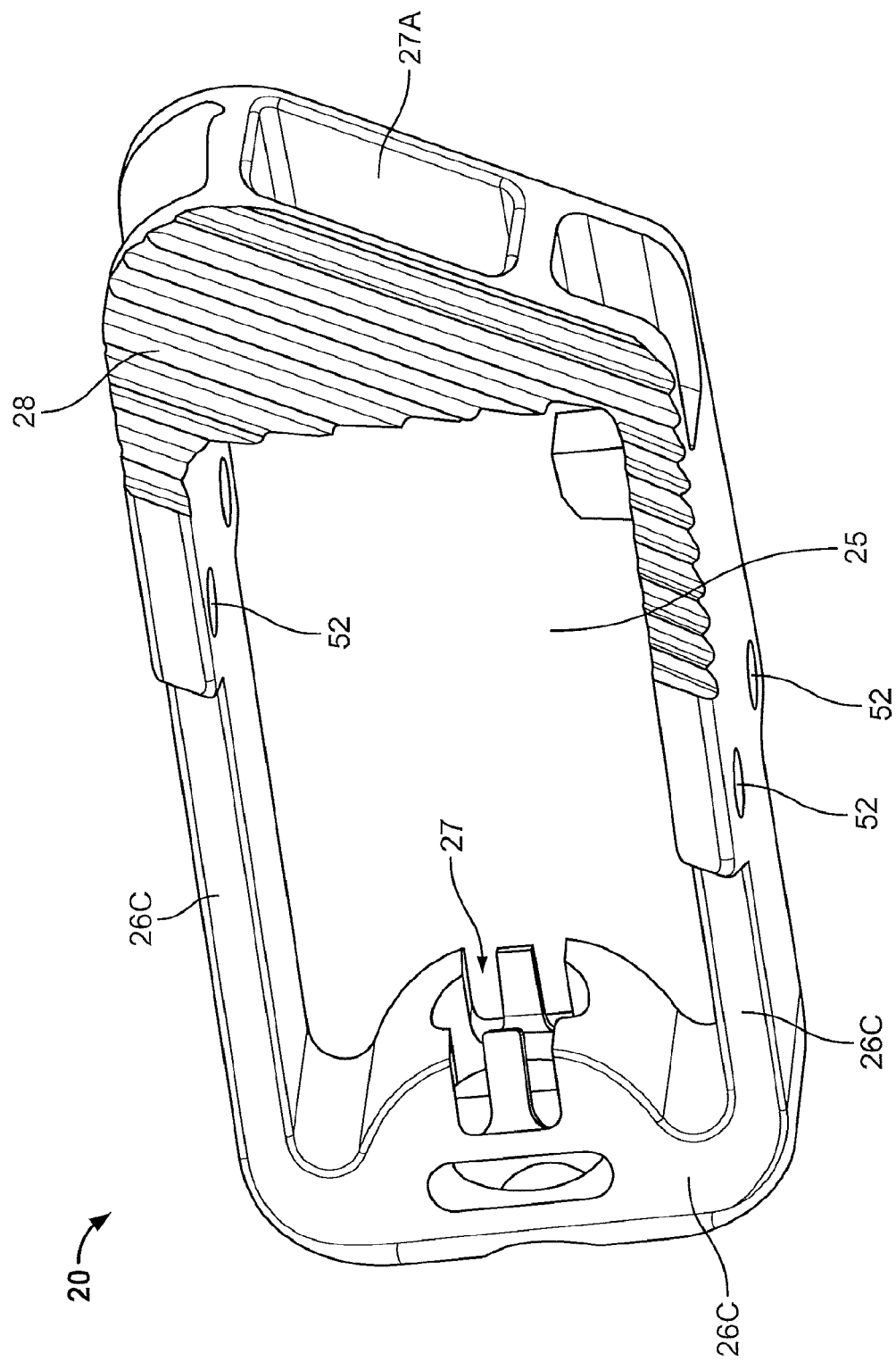
FIG. 4 shows yet another alternate embodiment of the housing of the expandable spinal implant disclosed herein.
Figure 5:
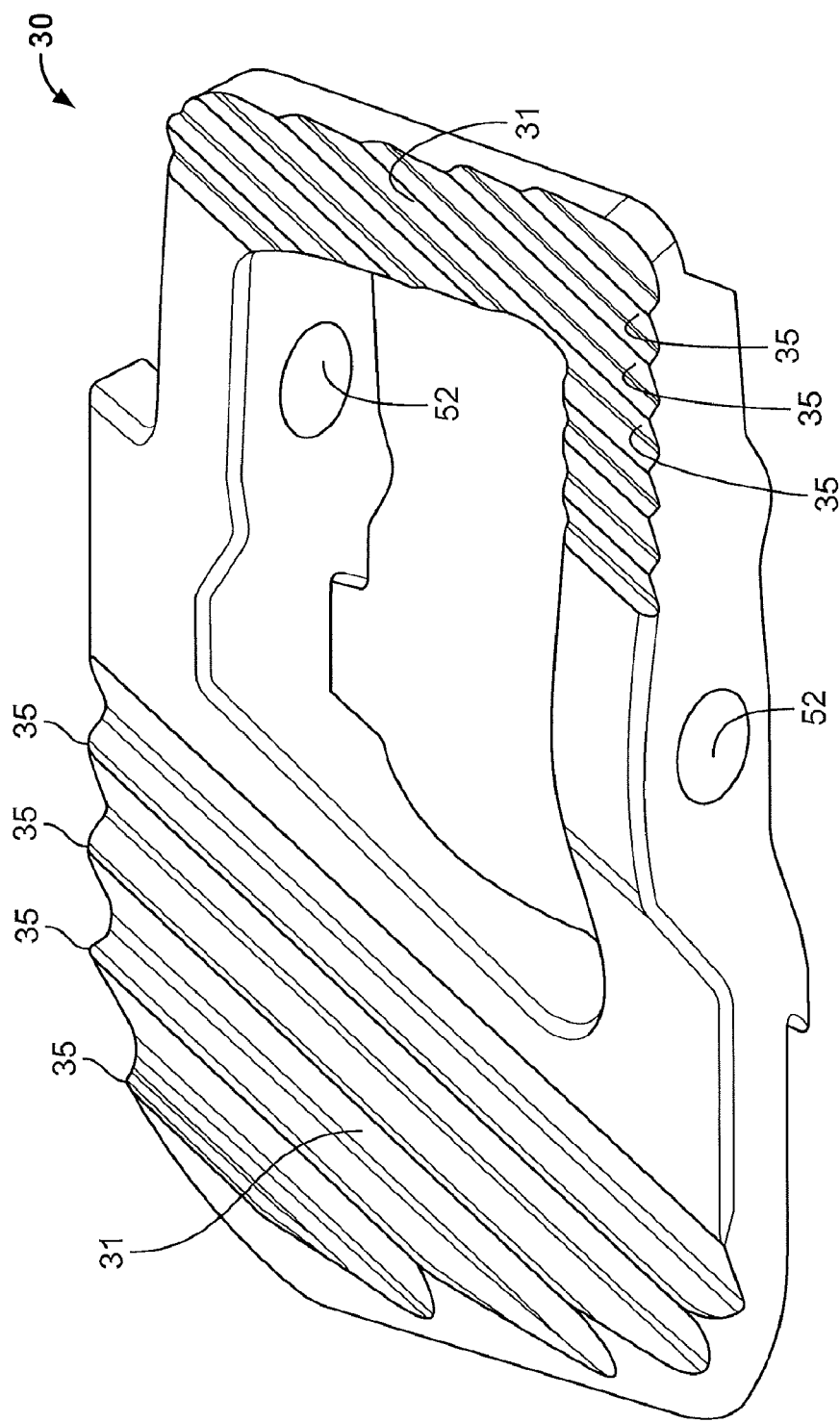
FIG. 5 shows a top view of the outer surface of one embodiment of the top moveable endplate of the expandable spinal implant of present disclosure.
Figure 6:
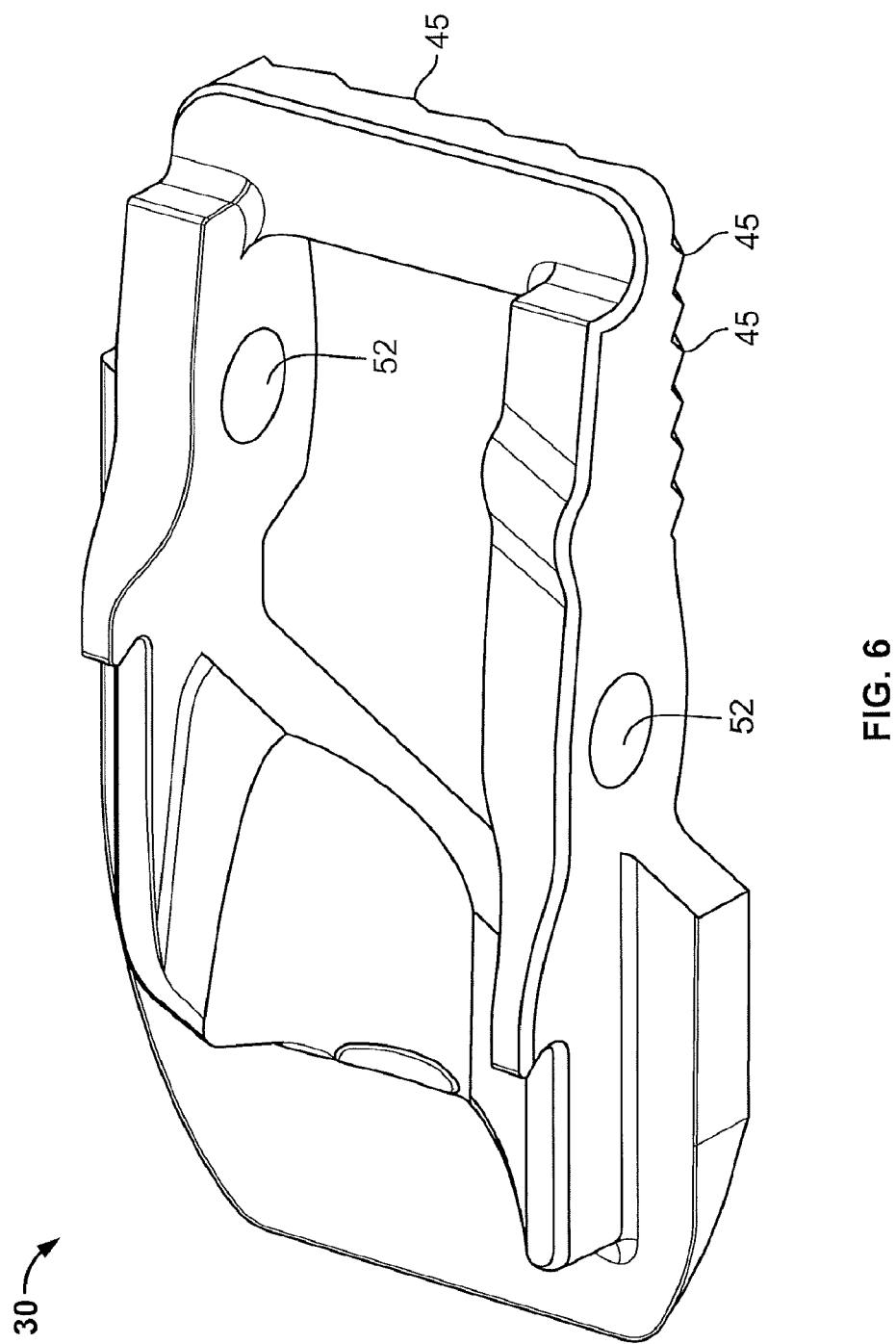
FIG. 6 shows a top view of the inner surface of one embodiment of the bottom moveable endplate of the expandable spinal implant of the present disclosure.
Figure 7A:
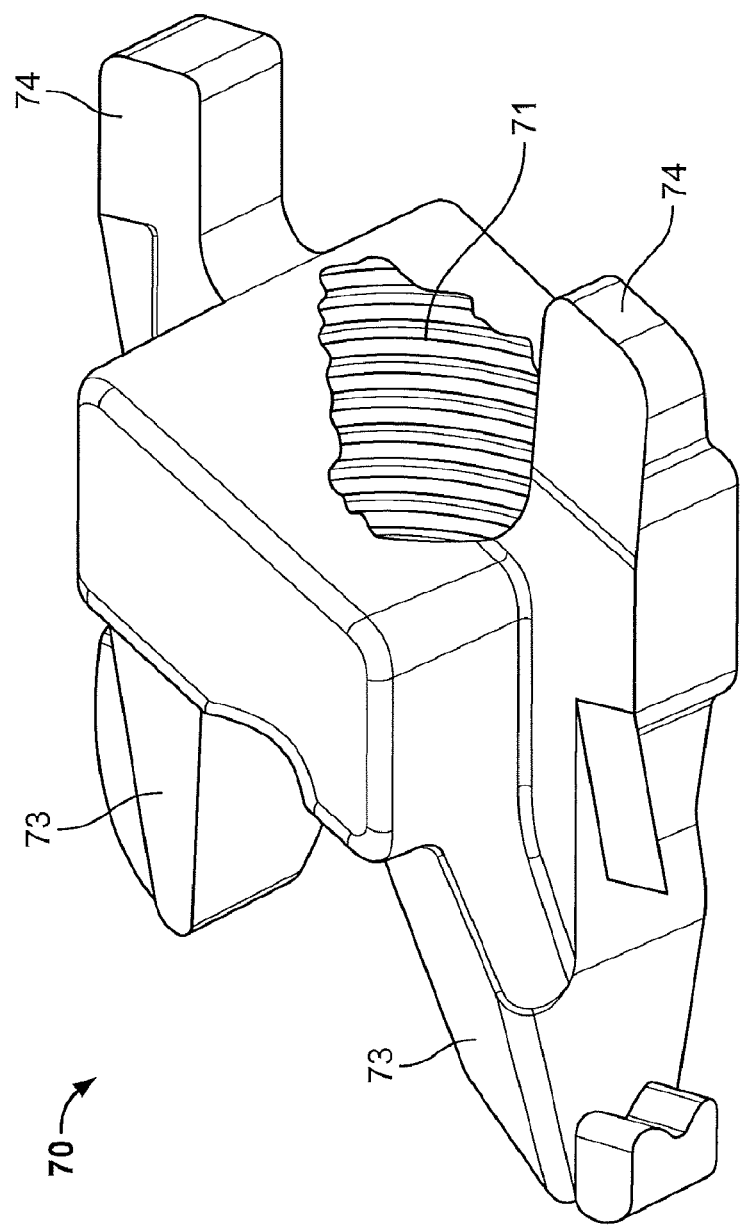
FIGS. 7A-7C show a perspective view, top view and side view of one embodiment of the central body of the expandable spinal endplate of the present disclosure.
Figure 7B:
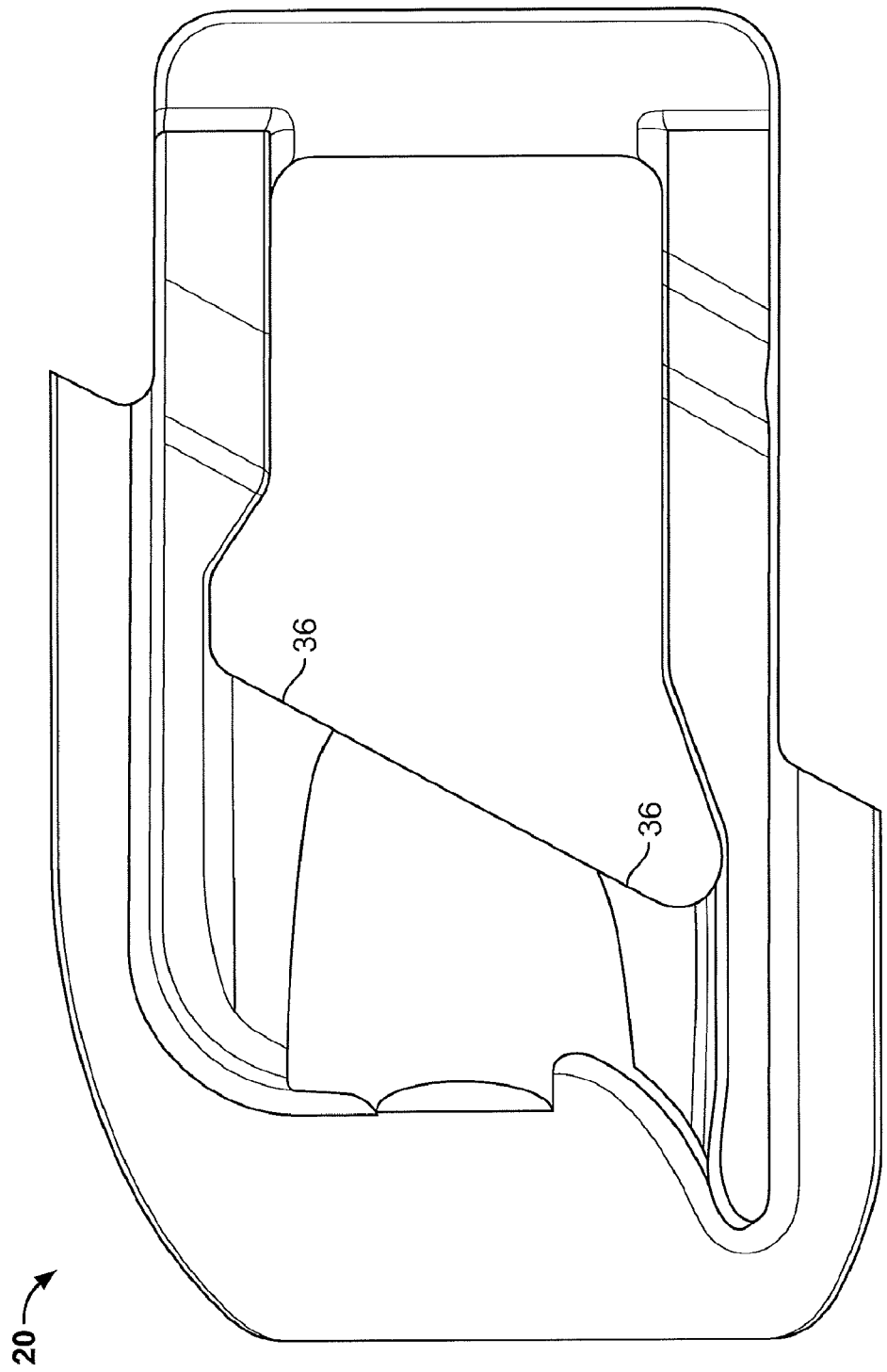
Figure 7C:
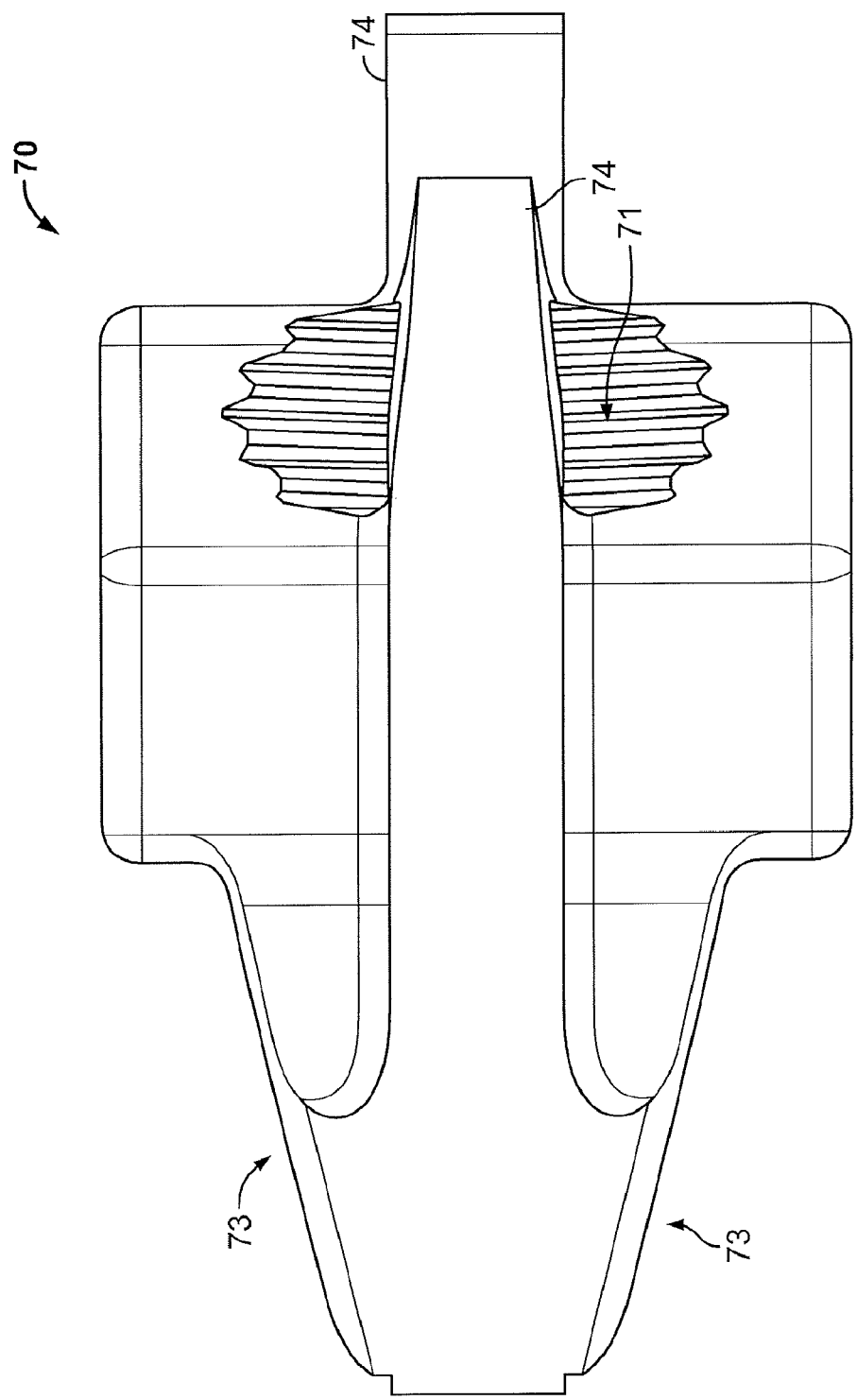
Figure 7D:
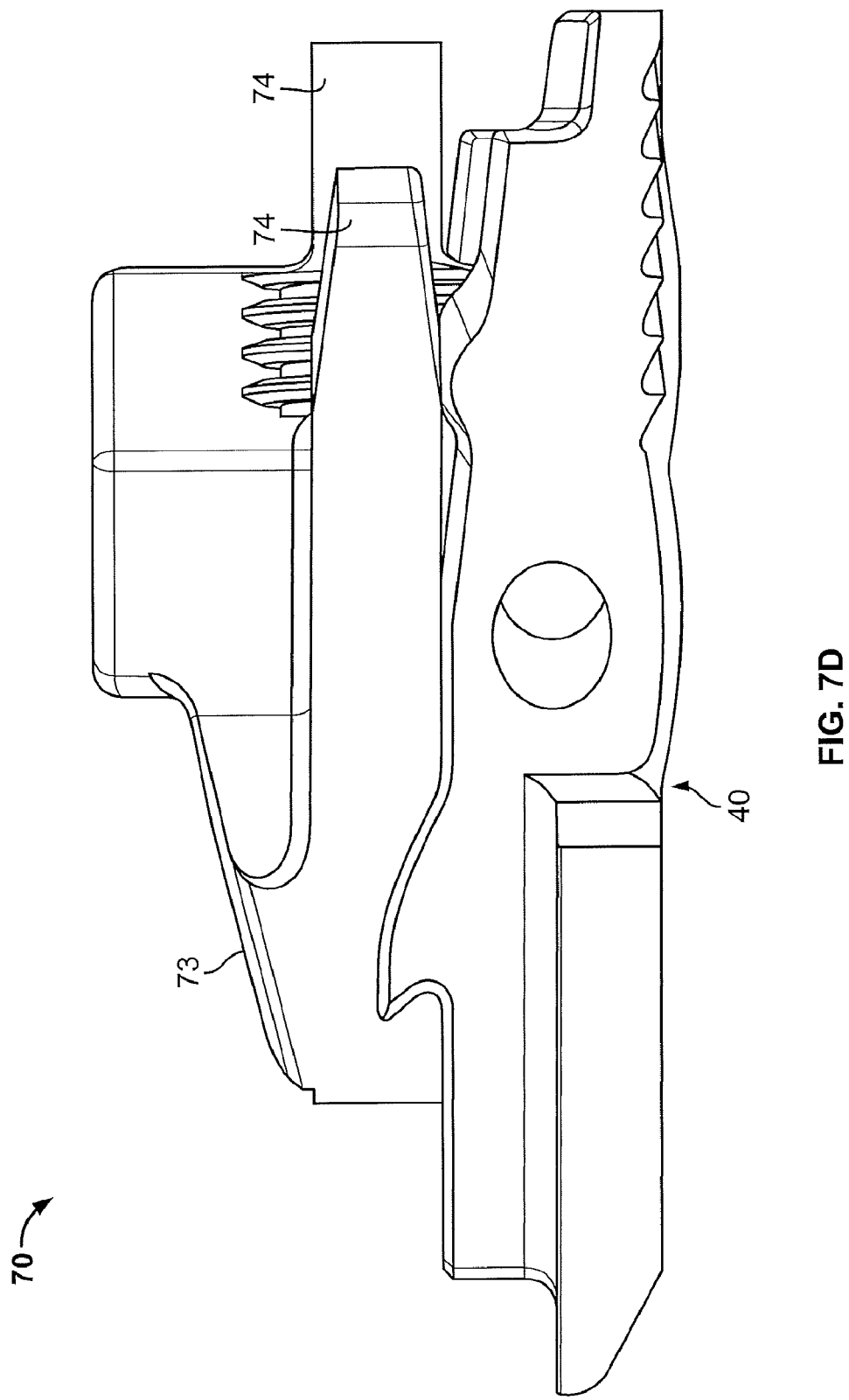
FIG. 7D shows a side view of one embodiment of the central body and lower moveable endplate of the expandable spinal implant of the present disclosure together.
Figure 8:
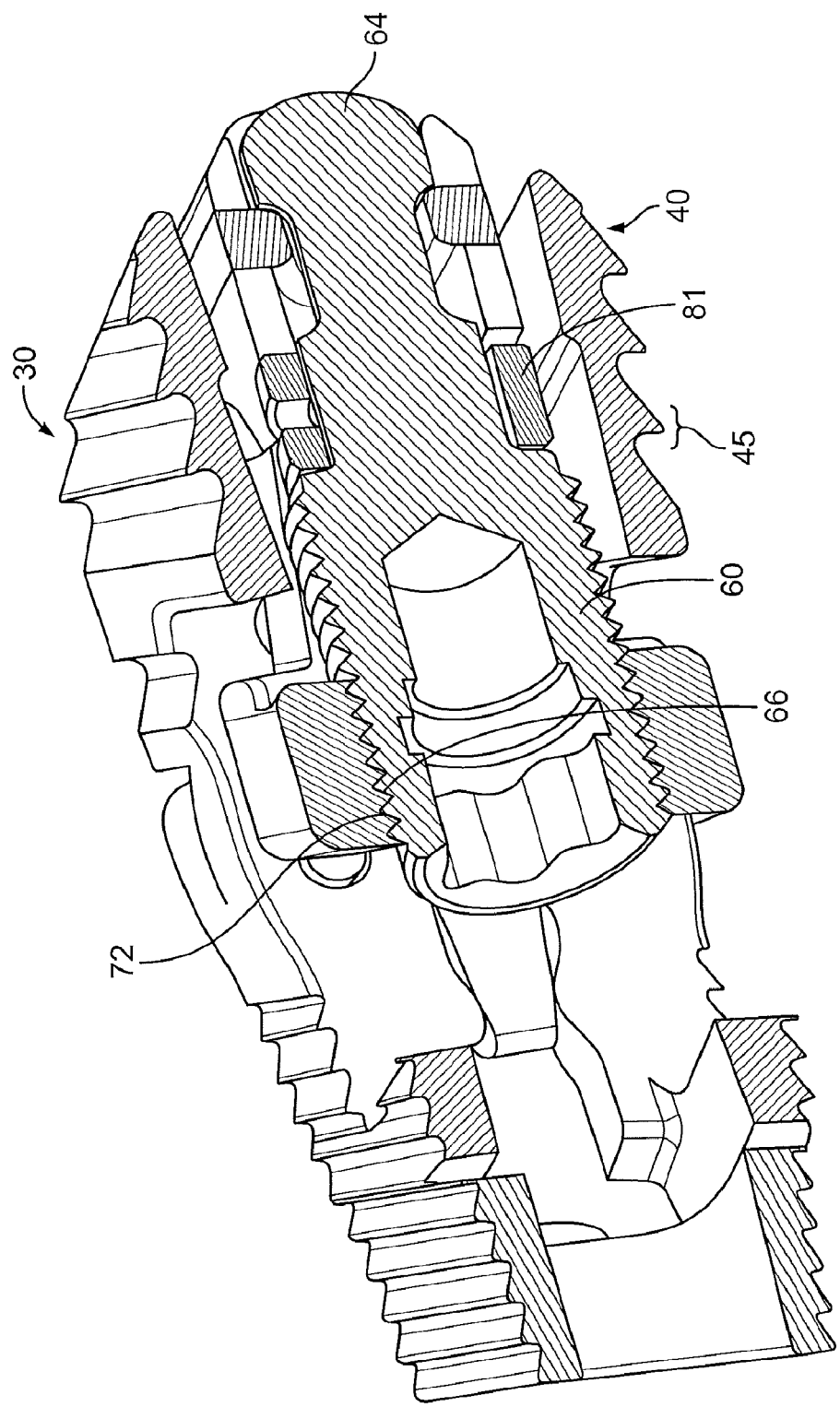
FIG. 8 shows a cross sectional view of one embodiment of the expandable spinal implant of the present disclosure.
Figure 9:
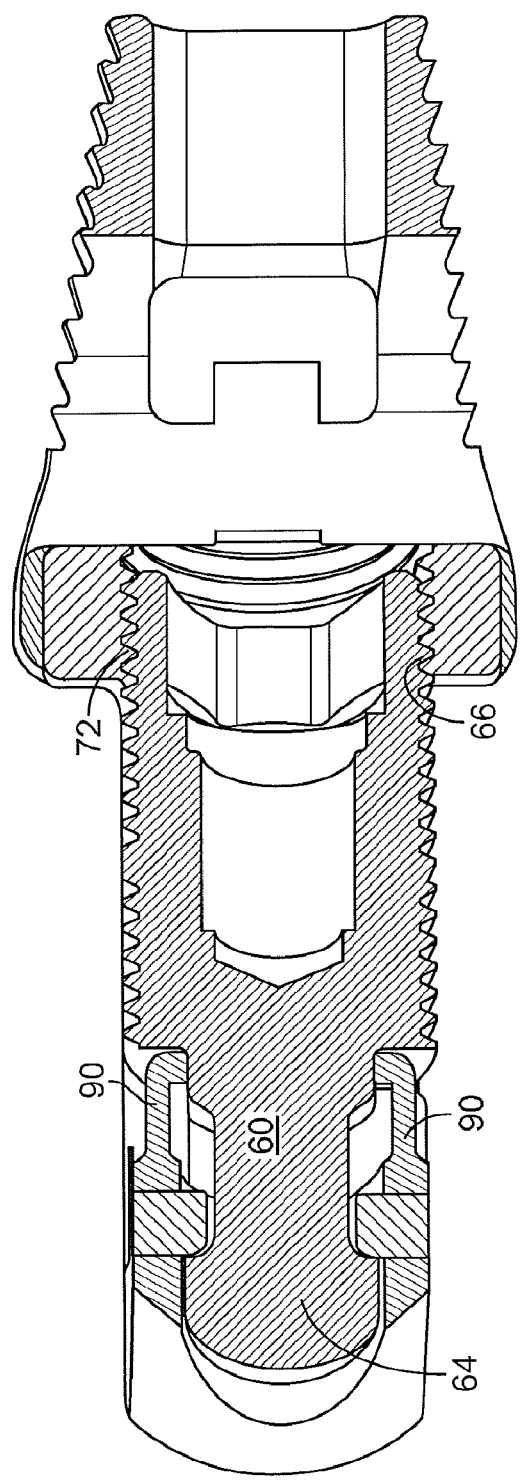
FIG. 9 shows a cross sectional view of an alternate embodiment of the expandable spinal implant of the present disclosure.
Figure 10:
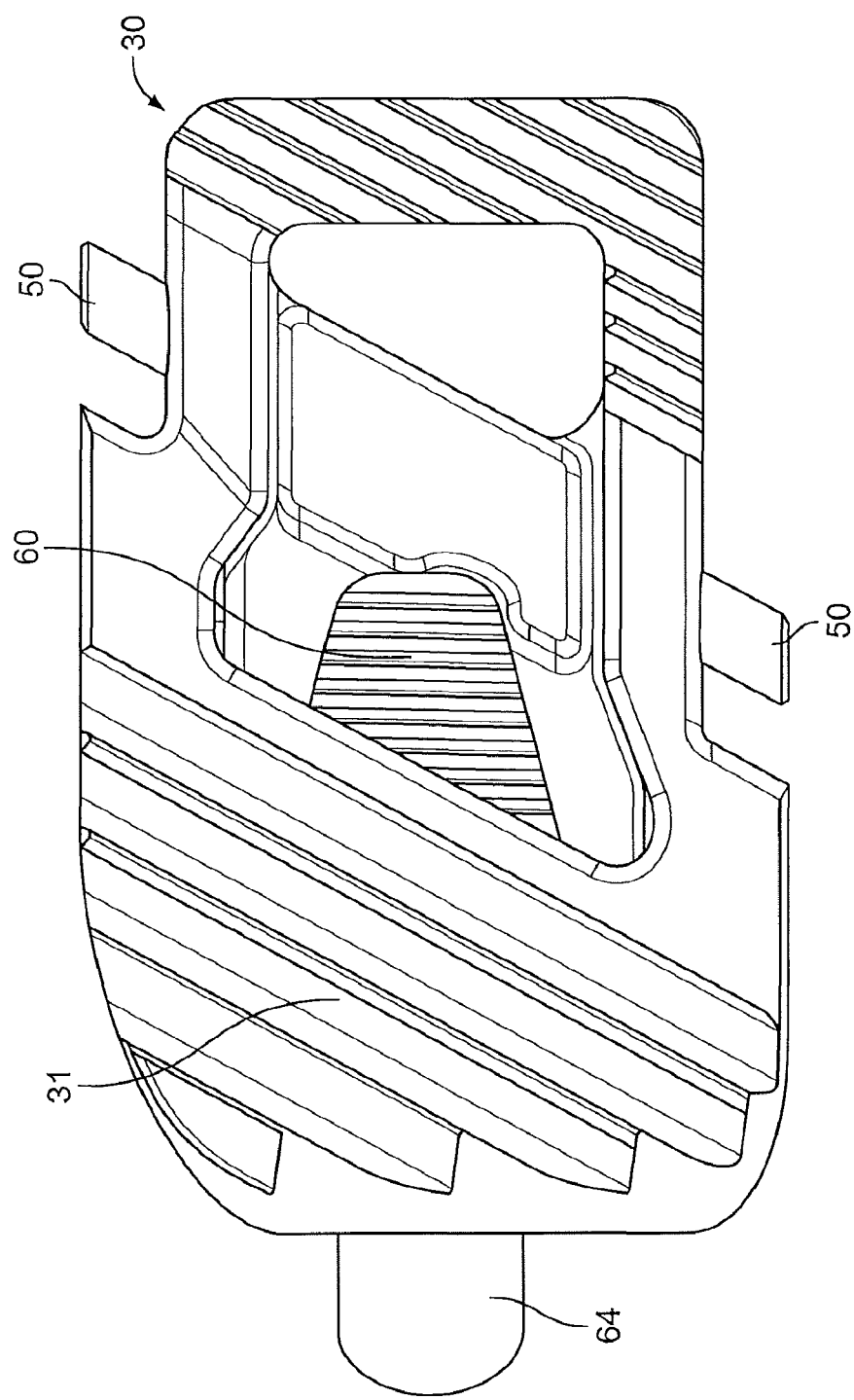
FIG. 10 shows a top view of one embodiment of the lead screw, central body and top moveable endplate of the expandable spinal implant of the present disclosure.
Figure 12:
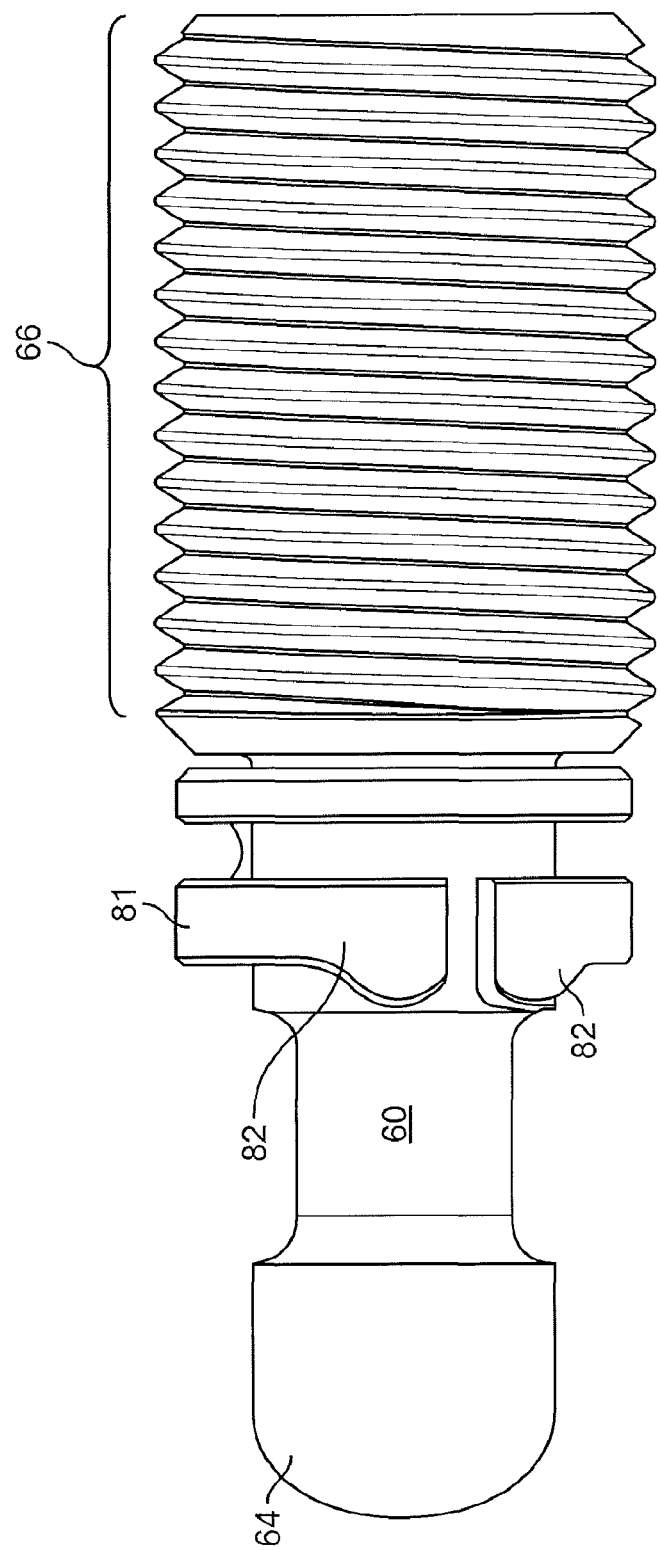
FIG. 12 shows one embodiment of the locking collar positioned onto a lead screw of the present disclosure.
Figure 13:
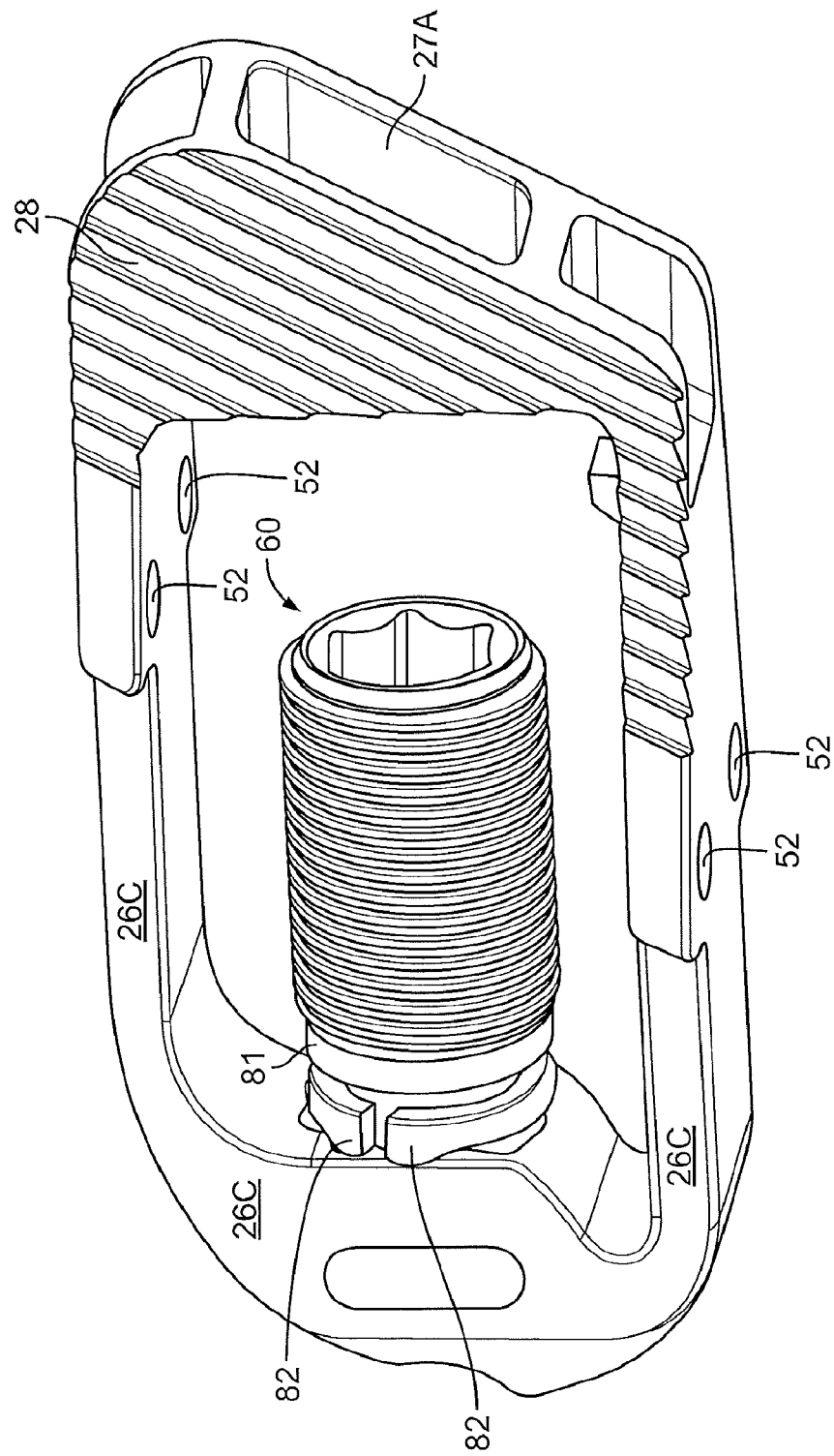
FIG. 13 shows one embodiment of the lead screw inserted into the housing.

The housing 20 may also comprise a recessed deck formed by a flat surface 26C. The recessed deck is configured to receive the upper and lower moveable endplates 30, 40 when the implant is in the collapsed configuration. The recessed deck is offset vertically towards the interior of the housing 20 from the fixed horizontal sections 28 and the vertical distance between the fixed horizontal section 28 and the flat surface 26C may be spanned by a ledge 26 as shown in FIGS. 2-4. In embodiments with the recessed deck, the housing 20 may also include a ramp 26B and a lip 26C on the tapered first end wall 22 of the implant 10. The ramp 26B and lip 26c serve to aid in the insertion of the implant 10 into the disc space while preventing tissue or other unwanted material from working its way into the space between the flat surface 26C and the upper and lower moveable endplates 30, 40.

As will be discussed in more detail below, the housing 20 also comprises portions of the passive locking mechanism as shown in FIGS. 2-4.

The implant 10 also includes upper and lower moveable endplates 30, 40. In the exemplary embodiment shown in FIGS. 1-19 and especially FIGS. 5-6, the upper and lower endplates 30, 40 are mirror images of one another, though it is contemplated that the upper and lower endplates may each have unique structural features. The upper and lower moveable endplates 30, 40 have bone contact surfaces 31, 41 which contact the vertebral bodies adjacent the disc space in which the implant 10 is inserted. The bone contact surfaces 31, 41 have anti-migration features 35, 45 which aid in preventing the implant 10 from shifting after insertion. The anti-migration features 35, 45 may be teeth as depicted herein and may also be treated (for example, through a sandblasting type procedure) that serves to produce a coarse or rough surface on the anti-migration features 35, 45 to encourage bone growth. The upper and lower moveable endplates 30, 40 are pivotable relative the housing 20 via the turning of the drive screw 60.

The upper and lower moveable endplates 30, 40 are pivotably connected to the housing 20 through pins 50 which pass through pin holes 52 in the housing 20 and the upper and lower moveable endplates 30, 40. In its collapsed configuration, the upper and lower moveable endplates 30, 40 lie flat or nearly flat in the recessed deck of the housing 20 on the flat surface 26C to aid in the insertion of the implant 10 into the disc space. For example, as shown in FIGS. 1-6, the upper and lower moveable endplates 30, 40 rest on flat surface 26C such that in the collapsed configuration the upper and lower moveable endplates 30, 40 are in horizontal alignment with the fixed horizontal sections 28. As the upper and lower end plates 30, 40 pivot relative to the housing 20, the angle of lordosis increases. In one embodiment, the implant 10 may provide between 1 and 40 degrees of lordosis.

The implant 10 also has a central body 70 between the upper and lower moveable endplates 30, 40 and at least partially surrounded by the housing 20. The central body 70 comprises a lead screw aperture 71 which is in vertical and horizontal alignment with the aperture 27 on the first end wall 23. The lead screw 60 may be inserted through the aperture 27 on the first end wall 23 until the rounded end 64 rests against, or abuts, the aperture 27 and the opposite end of the lead screw 60 is in the lead screw aperture 71 which comprises threads 72 complimentary to the threads 66 on the lead screw 60. The end of the lead screw 60 in the lead screw aperture 71 may comprise either a socket or other mechanism (such as a slotted or cross screwdriver head configuration) that can be connected to the insertion tool 100 through which the manipulation of the insertion tool 100 causes the lead screw 60 to turn. This end of the lead screw 60 is accessible via aperture 27A.

As the lead screw 60 turns in either the clockwise or counter-clockwise direction, the threads on the central body 70 cause the central body 70 to move laterally either towards the first end wall 23 or the second end wall 24 of the implant 10. In one embodiment, turning the lead screw 60 clockwise causes the central body 70 to move laterally towards the first end wall 23 while turning the lead screw 60 counterclockwise causes the middle wall 70 to move laterally towards the second end wall 24 away from the first end wall 23.

As the central body 70 moves, wedges 73 contact ramps 36 on the interior surface of the upper and lower moveable endplates 30, 40 and cause the upper and lower endplates 30, 40 to rise outwardly away from the central body 70 (in other words, the upper and lower moveable endplates 30, 40 move towards the vertebral bodies above and below the disc space in which the implant has been inserted). Eventually, implant 10 is expanded the amount desired to restore the height of the intervertebral disc space. FIGS. 14-18 show the movement of the various parts of the implant 10 as it moves from the collapsed configuration to the expanded configuration.

Figure 14:
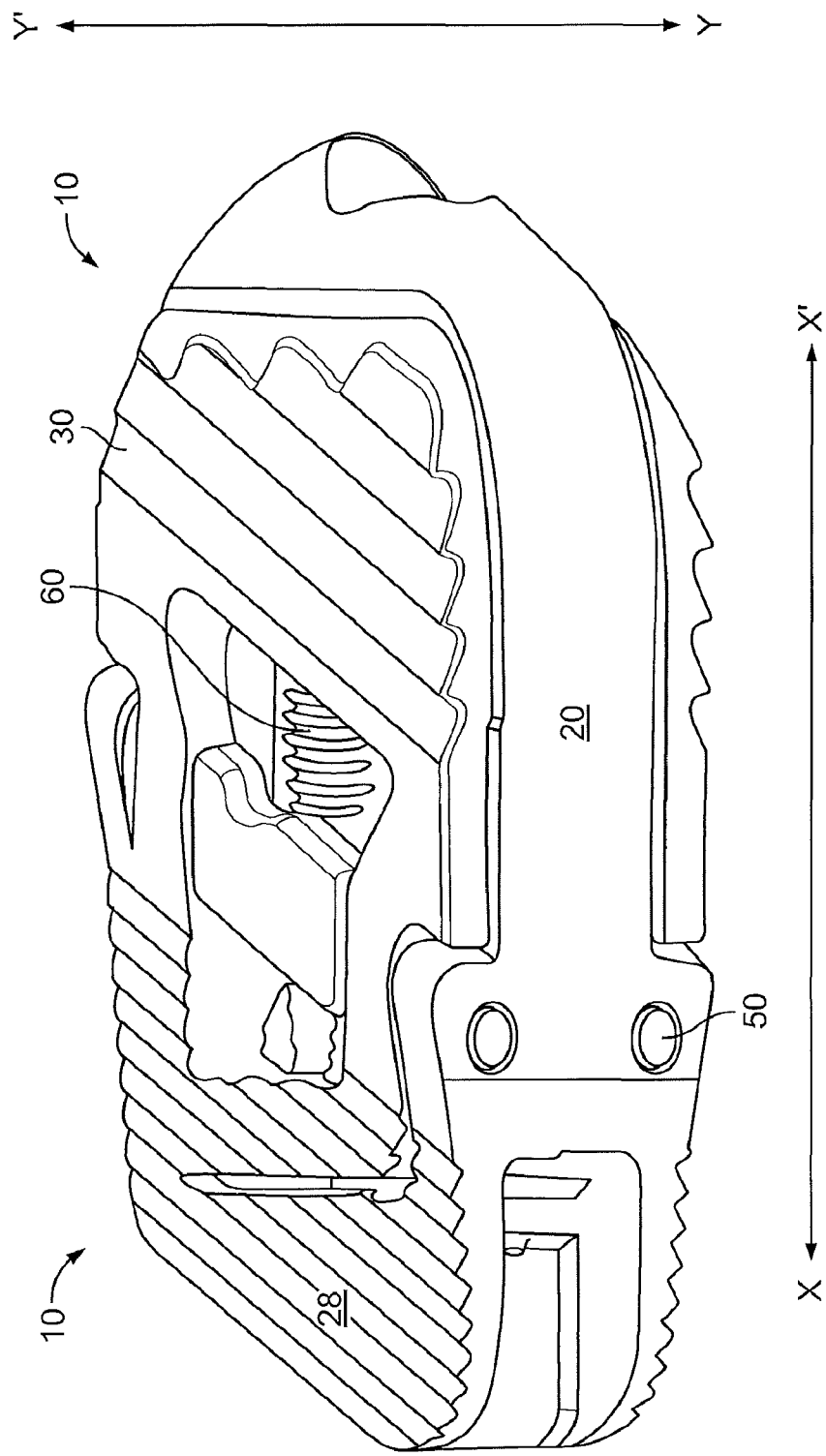
FIGS. 14-17 show perspective and cross sectional views of one embodiment of the expandable spinal implant of the present disclosure in the expanded and collapsed configurations.
Figure 15:
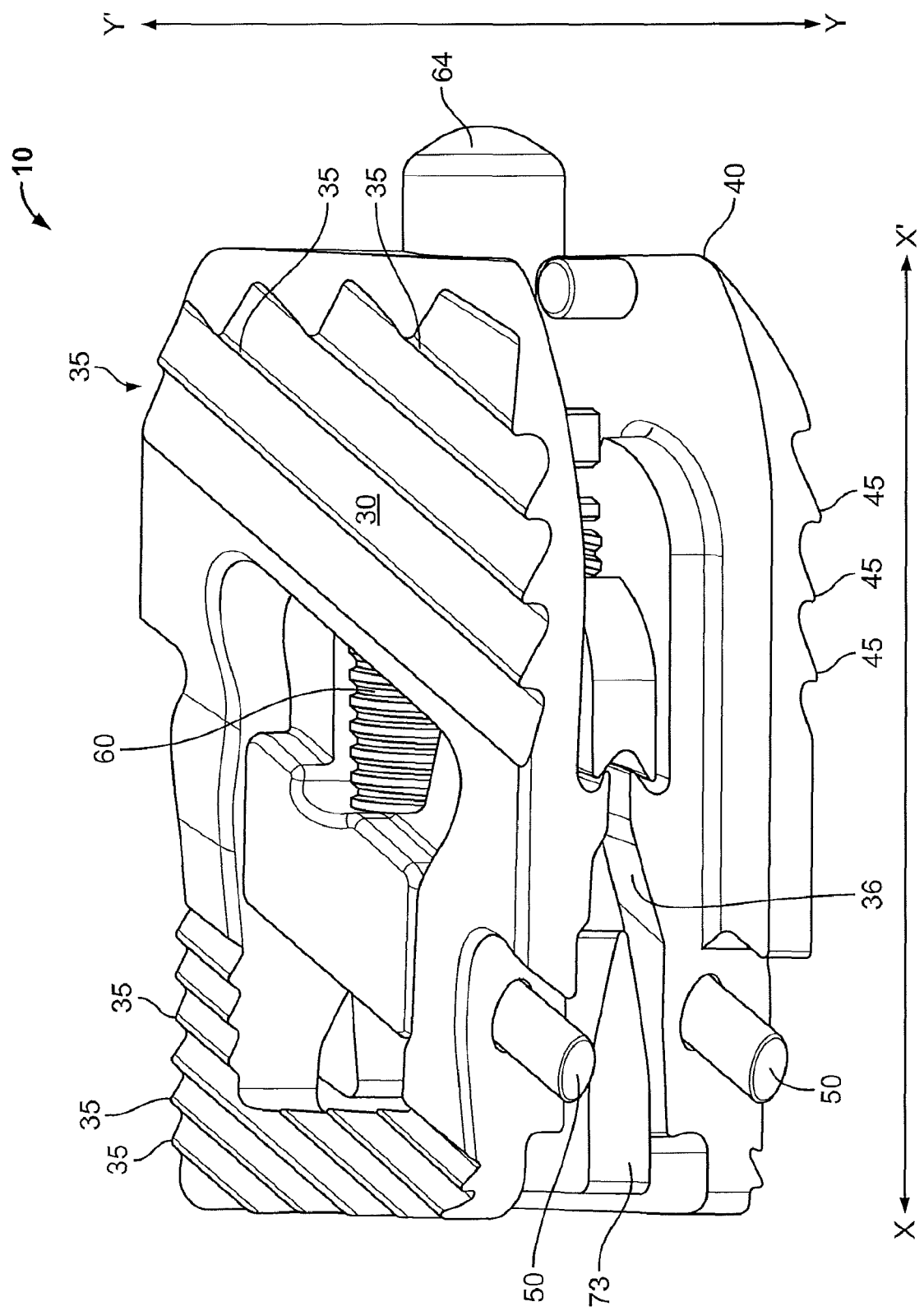
Figure 16:
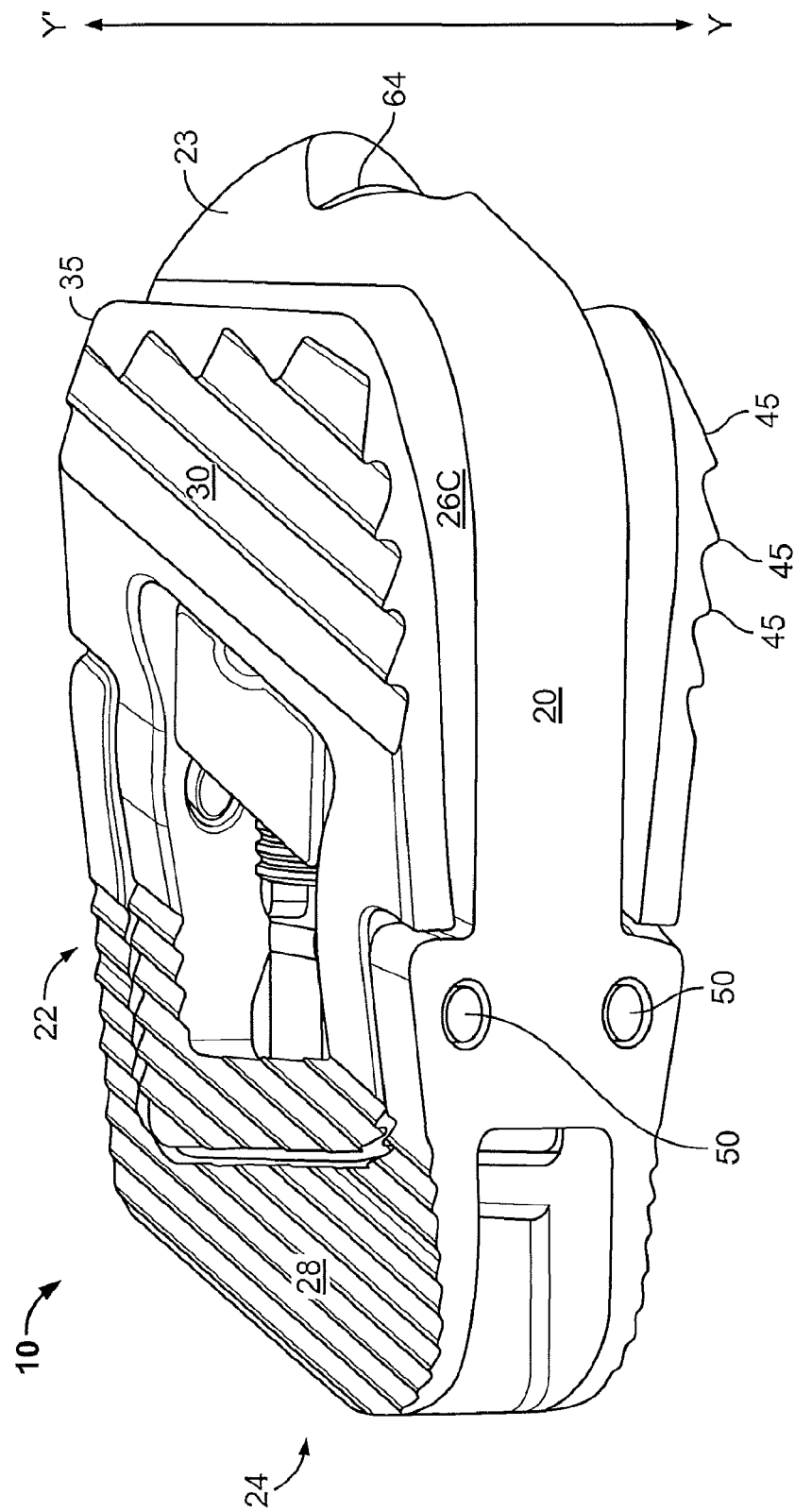
Figure 17:
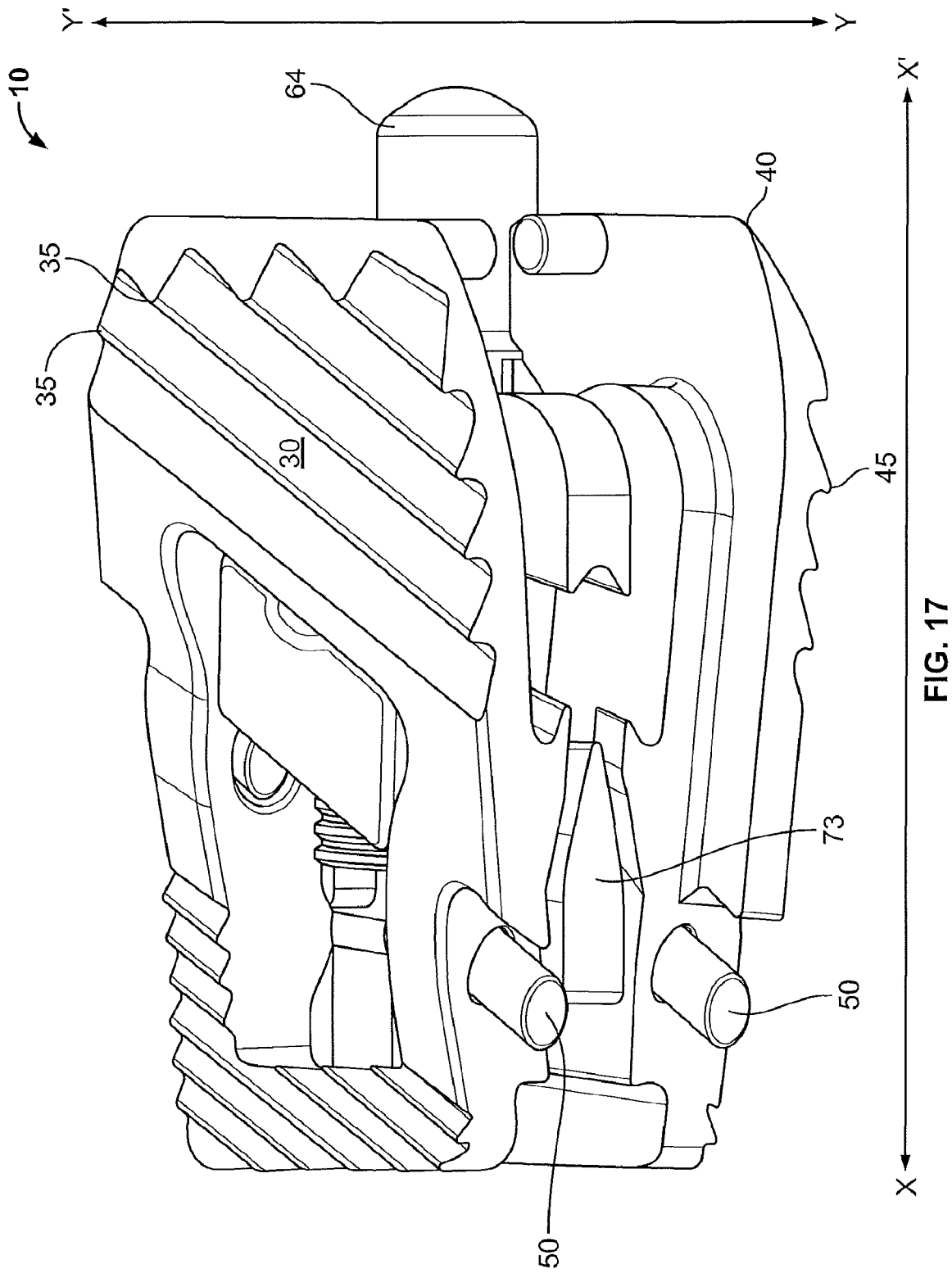
Figure 18:
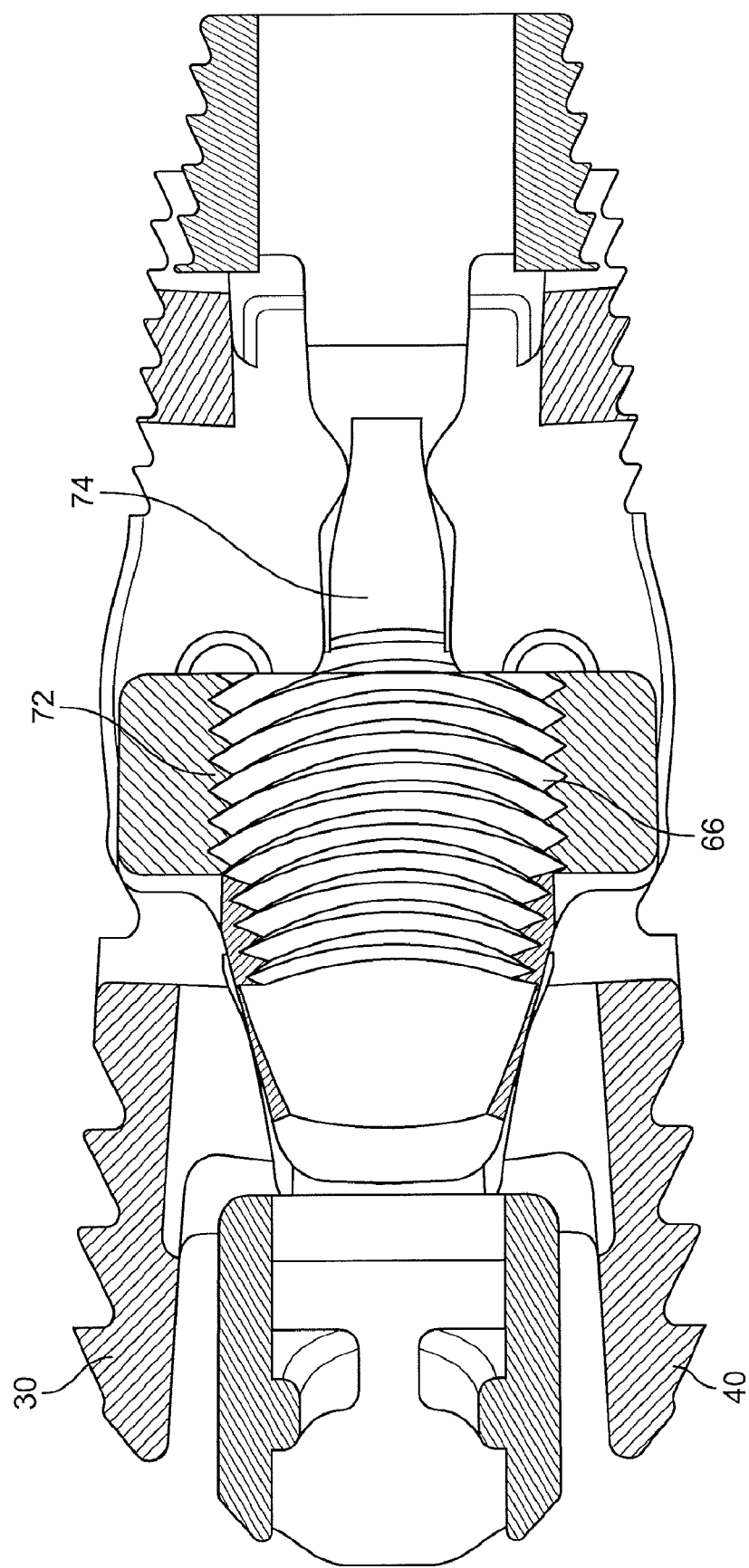
FIG. 18 shows an alternate cross section view of the expandable spinal implant of the present disclosure in the expanded configuration.
Figure 19:
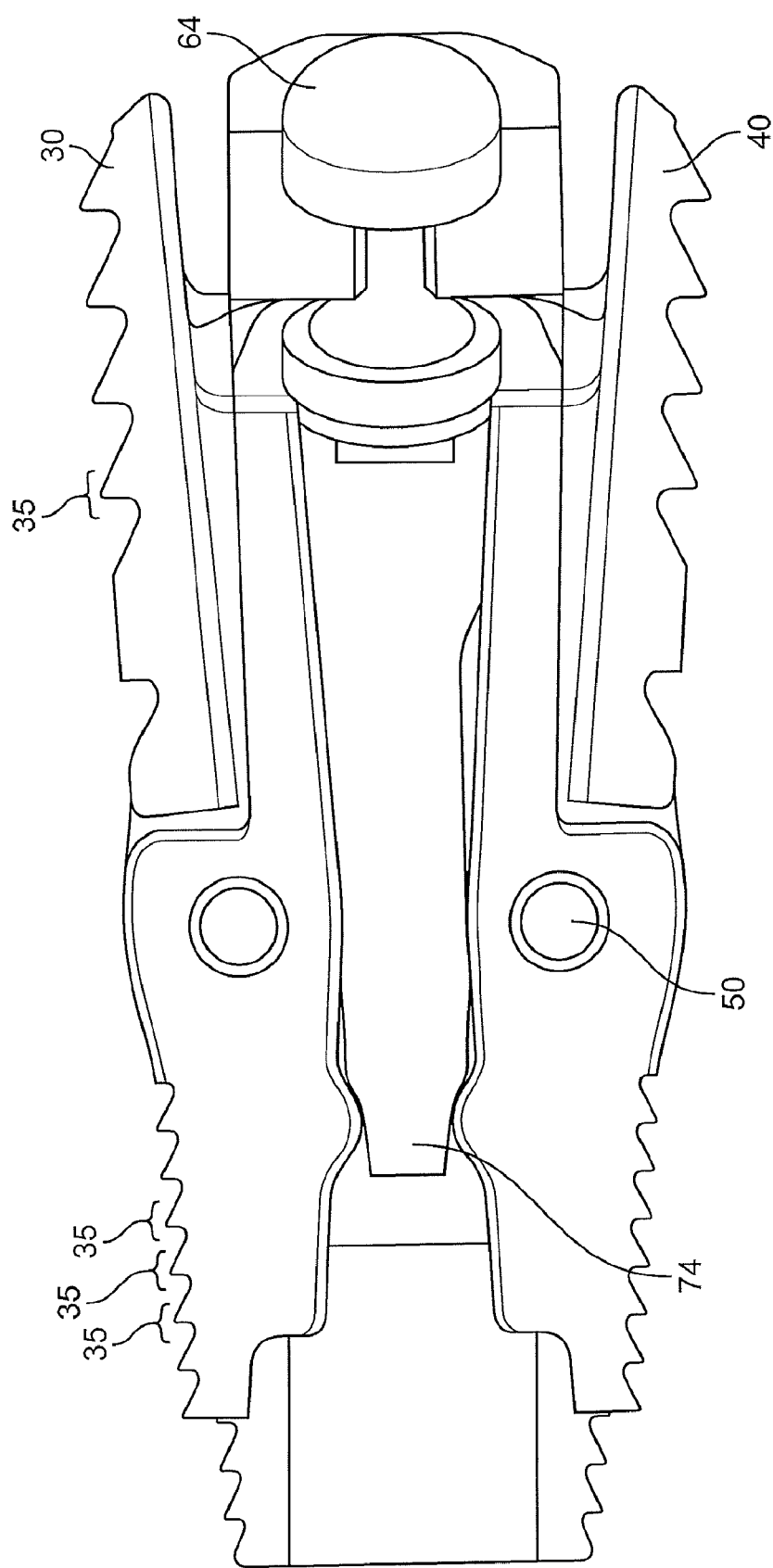

FIG. 14 shows the implant 10 in the collapsed configuration ready for insertion along line x-x' into a disc space. FIG. 15 shows the same view of the implant as FIG. 14, but the housing 20 is not shown. In FIG. 15, the wedges 73 have not moved along the axis of line x-x' and therefore the upper and lower moveable endplates 30, 40 have not moved vertically along line y-y'. FIGS. 16 and 17 are similar views of the implant 10 as FIGS. 14 and 15, but the implant 10 is in the expanded configuration. As shown in FIGS. 16 and 17, in the expanded configuration the moveable upper and lower endplates 30, 40 have moved vertically along line y-y' by the movement of wedges 73 against ramps 36 along line x-x'.

Now referring to FIGS. 3-4 and 5-13, the implant 10 may also comprise a passive locking mechanism 80. As the patient returns to normal activity, the implant 10 will be subjected to forces and strains that could cause the lead screw 60 to back out thereby allowing the implant 10 to collapse as either the upper moveable endplate 30, the lower moveable endplate 40 or both retract from their extended position. The passive locking mechanism 80 prevents the lead screw 60 from working loose or backing out. There are several embodiments of the passive locking mechanism 80 contemplated by this disclosure.

In a first embodiment shown in FIGS. 11A-13, the passive locking mechanism comprises a locking collar 81 that is fitted to one end of the lead screw 60. The locking collar 81 is then positioned between the threads 66 of the lead screw 60 and the first end wall 23 where the lead screw 60 passes through the aperture 27. The locking collar 81 comprises one or more recess engagement tabs 82 that engages one or more recesses 83 (shown in FIG. 3) present on the interior surface of the first end wall 23 surrounding aperture 27. The one or more recess may be spaced evenly around the aperture 27. In one embodiment, the implant 10 comprises between two and twenty recesses 83. In alternate embodiments, the implant 10 comprises between eight and twelve recesses 83.

The locking collar 81 is affixed to the lead screw 60 so that as the lead screw 60 turns, the locking collar 81 also turns. As the amount of force applied to the lead screw 60 by the surgeon during implantation increases to an amount sufficient to cause the one or more recess engagement tabs 82 to be displaced from the one or more recesses 83, the one or more recess engagement tabs 82 will rotate towards the next recesses 83 until the one or more recess engagement tabs 82 settle or fall into the next recesses 83. If the surgeon then stops turning the lead screw 60 the locking collar 82 will stop turning as well. In this embodiment of the passive locking mechanism 80 the fitment of the one or more recess engagement tabs 82 into the one or more recesses 83 prevents the lead screw 60 from backing out as the forces and strains imparted on the locking collar 82 via the lead screw 60 through normal everyday patient activity will not be great enough to overcome the force securing the one or more recess engagement tabs 82 into the one or more recesses 83 and thus the lead screw 60 is locked in place.

In an alternate embodiment of the passive locking mechanism 80 shown in FIGS. 4 and 11B, the lead screw 60 comprises a lead screw collar 68 positioned between the rounded end 64 and the threads 66 which comprises one or more recesses 69 spaced round the lead screw collar 68. The interior surface of the first end wall 23 comprises the aperture 27 through which the lead screw 60 passes (as described above) and one or more extended arms 90 that extend from the first end wall 23 towards the center of the housing 20. The extended arms 90 comprise a recess engagement tab 91 with a bump that is configured to fit into the one or more recesses 69 on the lead screw collar 68. In a similar fashion to the first embodiment of the passive locking mechanism 80 described above, as the amount of force applied to the lead screw 60 by the surgeon during implantation increases to an amount sufficient to cause the one or more recess engagement tabs 91 to be displaced from the one or more recesses 69, the one or more recess engagement tabs 91 will rotate towards the next recesses 69 until the one or more recess engagement tabs 91 settle or fall into the recesses 69. In this embodiment of the passive locking mechanism 80 the fitment of the one or more recess engagement tabs 91 into the one or more recesses 69 prevents the lead screw 60 from backing out as the forces and strains imparted on the lead screw locking collar 81 via the lead screw 60 through normal everyday patient activity will not be great enough to overcome the force securing the one or more recess engagement tabs 91 into the one or more recesses 69 and thus the lead screw 60 is locked in place.

Additionally the implant 10 may comprise one or more anterior supports 74 on the central body 70. In order to achieve a successful surgical outcome in vertebral fusion surgeries, the amount of motion between the implant 10 and the adjacent vertebral bodies needs to be minimized—this may be accomplished by the use of screws, rods and/or plates as is well known in the art. Additionally, the motion within the implant 10 itself needs to be minimized as well. As discussed above, the one or more wedges 73 serve to either lift or lower the upper and lower moveable endplates 30, 40 and the one or more wedges 73 also provide support for the upper and lower moveable endplates 30, 40 to prevent them from collapsing. However, it may be advantage to provide a second means of support such as the one or more anterior supports 74 to prevent the upper and lower moveable endplates 30, 40 from pivoting around the one or more pins 50. The one or more anterior supports 74 extend axially from the central body (see, e.g., FIG. 7A) opposite the one or more wedges 73. When the upper and lower moveable endplates are raised and the implant 10 is in the expanded configuration, one end of the upper and lower moveable endplates 30, 40 will contact the one or more anterior supports thereby preventing the upper and lower moveable endplates 30, 40 from rotating about the pins 50 thus minimizing the amount of movement within the implant 10 after insertion.

Figure 20:
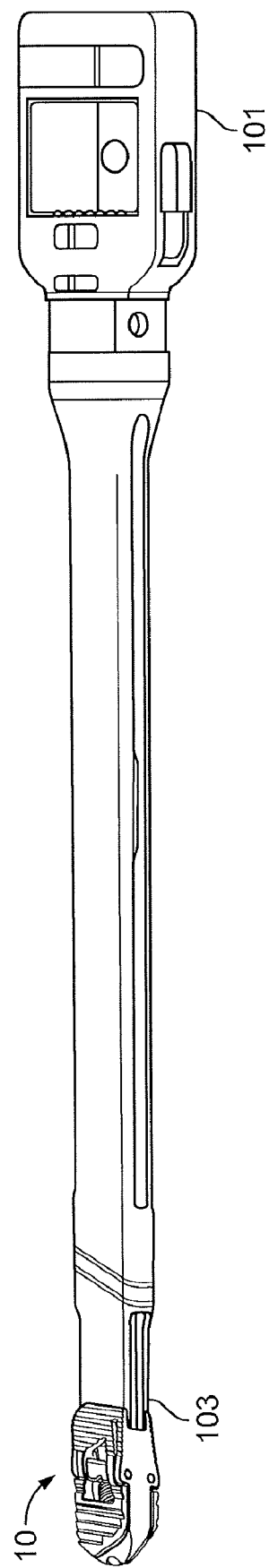
FIGS. 20 and 21 show one embodiment of the insertion tool of the present disclosure.
Figure 21:
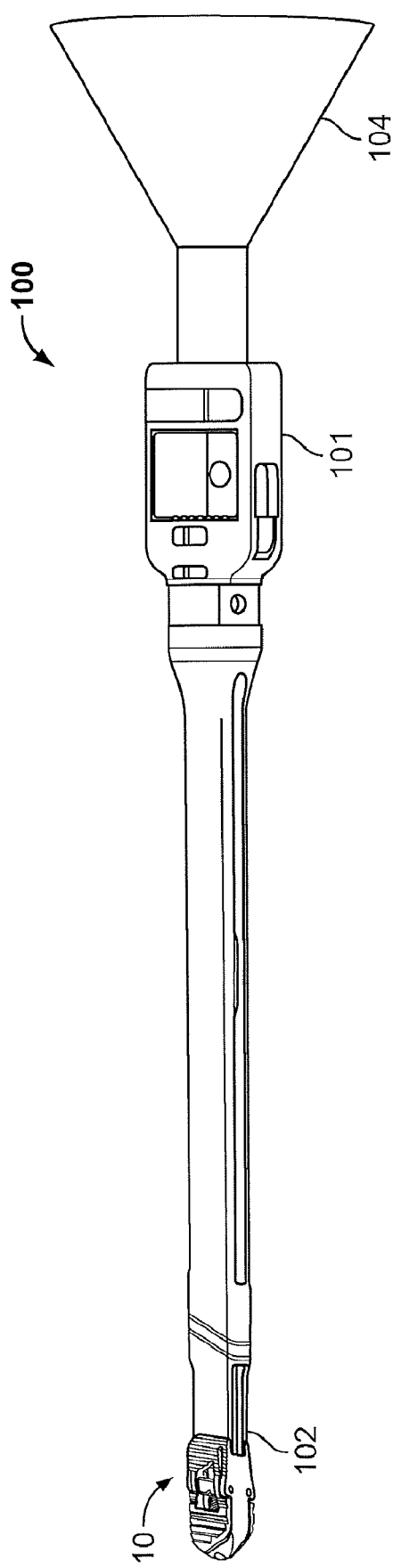
Figure 22:
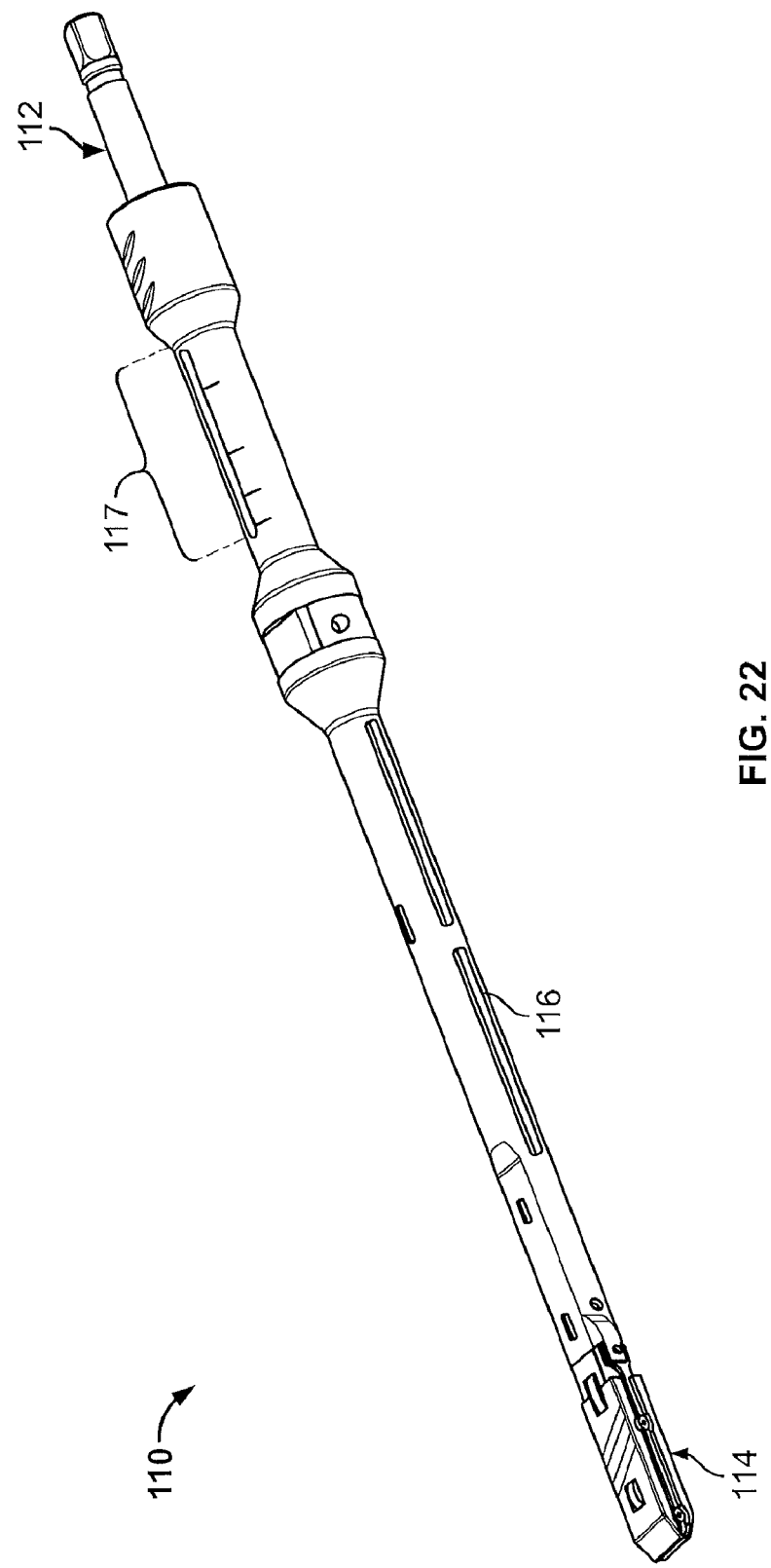
FIGS. 22-25 show various views of the measurement tool of the present disclosure.
Figure 23:
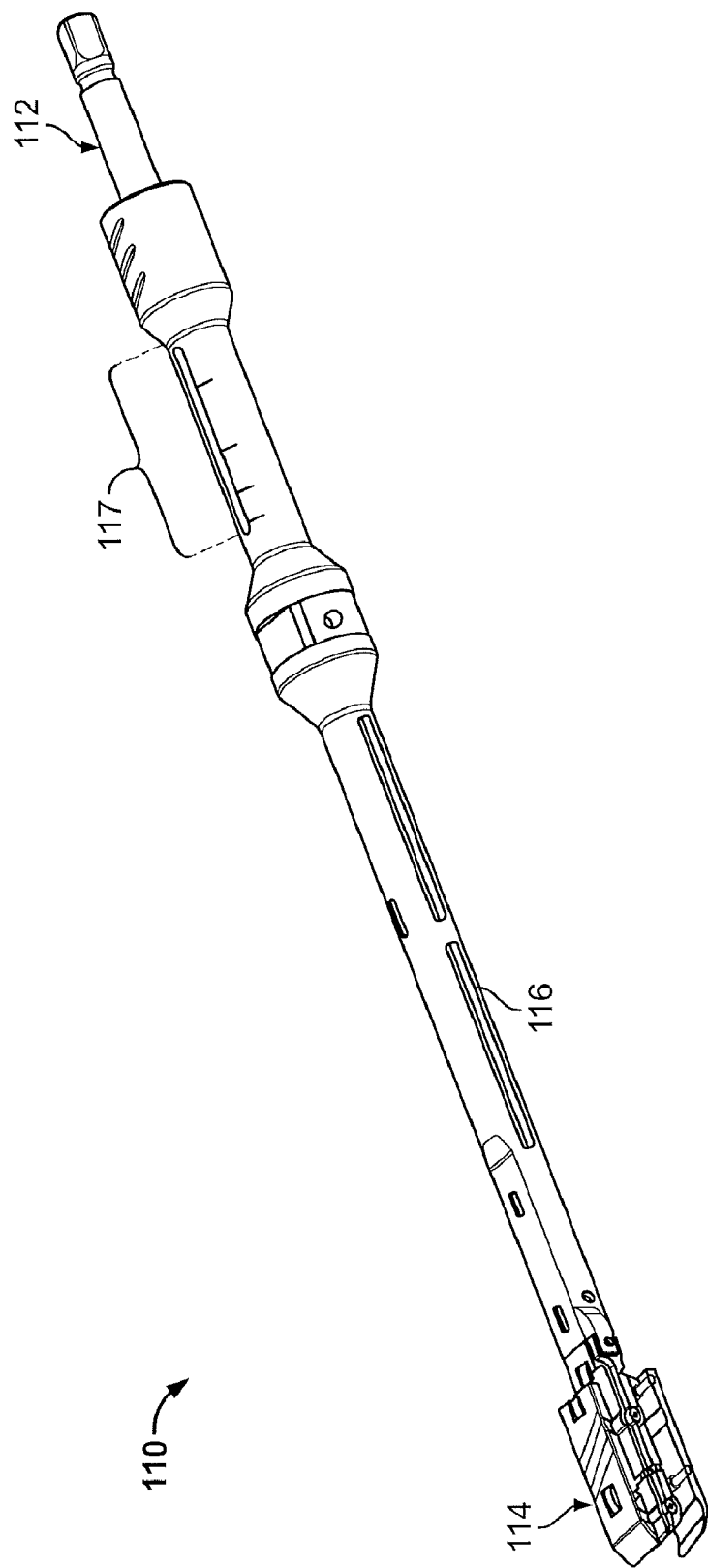
Figure 24:
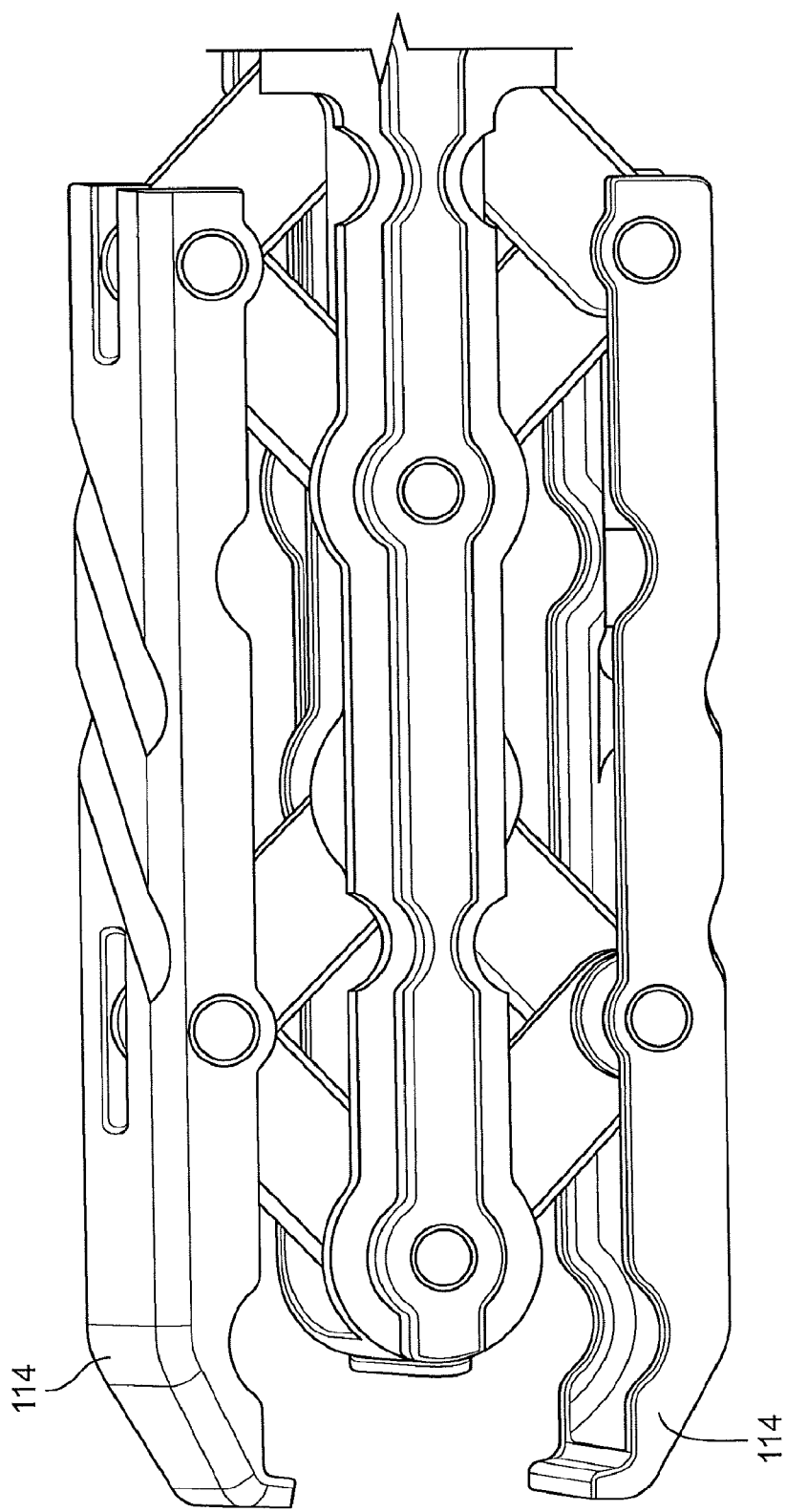
Figure 25:
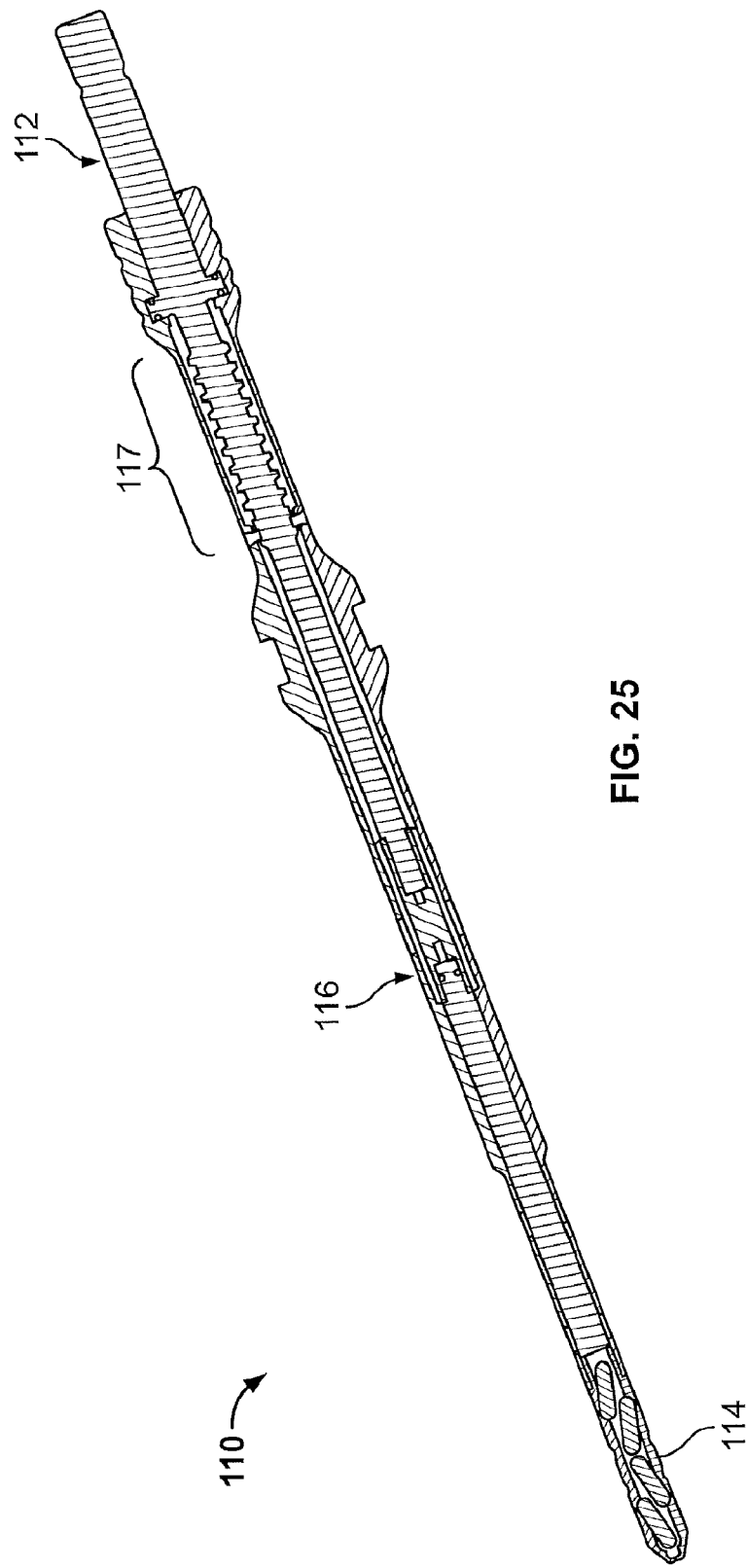

The present disclosure also provides an insertion tool 100, as shown in FIGS. 20 and 21, that engages with the implant 10 and aids in the insertion of the implant 10 during surgery. The insertion tool 100 comprises a rotatable element 101 in the end opposite the attachment point 102 with the implant 10. The rotatable element 102 may be in communication with the implant and specifically the lead screw 60 so that as the rotatable element 101 is rotated by the surgeon the lead screw 60 likewise rotates thus translating the wedges 73 and moving the upper and lower moveable endplates 30, 40. The attachment point 101 serves to provide a reversible, yet secure means of attaching the implant 10 to the insertion tool 100. The implant 10 may be attached to the insertion tool 100 prior to insertion of the implant between the vertebral bodies and may be unattached by the surgeon from the insertion tool 100 after insertion between the vertebral bodies. The means of attaching the implant 10 to the insertion tool 100 should allow the implant to be unattached from the insertion tool 100 quickly and easily so as to not disturb the implant after insertion.

The insertion tool 100 may comprise a hollow cylinder running its length. The hollow cylinder allows a surgeon to pack or insert bone graft composition into the fusion aperture 25 in the implant 10 after insertion and after the implant 10 is in its expanded configuration. As shown in FIG. 21, it may be desirable to use a funnel 103 to aid in the packing of the bone graft composition into the hollow cylinder of the insertion tool 100.

In another aspect, the present disclosure provides a measurement tool 110 useful for determining the approximate height required by the implant 10 upon insertion between vertebral bodies. One embodiment of this measurement tool is shown in FIGS. 22-25. The measurement tool comprises a first end 111 with a driver 112 and a second end 113 with two moveable endplates 114.

The driver 112 is rotatable and as it rotates, its rotational movement is translated by a series of linkages 115 located in the shaft 116 of the measurement tool 110 into a force that expands the moveable endplates 114. The endplates 114 at attached to a series of arms 117 which are in turn attached to the linkages 115. As the driver 112 rotates, the endplates 114 may be either raised away from the shaft 116 or lowered towards it.

The measurement tool 110 may also comprise an indicator feature 117 near the first end 111 that visually translates the movement of the endplates 114 into a series of predetermined units so that the surgeon can observe the movement of the endplates via the indicator feature 117. For example, the indicator feature may comprise an aperture on the shaft 116 that has a range of numbers from 1-10 printed (such as by laser printing) around the end of the aperture. As the endplates 114 are inserted between the vertebral bodies in their collapsed configuration, the indicator feature may have some marker correlating the height of the endplates 114 in the collapsed position to position "1" and as the endplates 114 are moved into their expanded configuration by the rotation of the driver 112, the marker may move from position "1" to position "2", "3", etc. The position numbers may then be correlated with the actual height of the endplates 114 providing the surgeon an estimate of the height of implant 10 for the particular patient's anatomy. Alternatively the numbers provided on the indicator feature 117 may directly provide the height of the endplates 114—in other words, the numbers may represent the height, in millimeters, of the endplates in the expanded configuration.

Although particular embodiments of the present disclosure have been described, it is not intended that such references be construed as limitations upon the scope of this disclosure except as set forth in the claims.

I claim:

1. An expandable spinal implant comprising:
   a plurality of moveable endplates pivotably connected to a housing;
   a central body located within the housing;
   a lead screw engaged with the central body; and
   a passive locking mechanism,
   wherein the passive locking mechanism comprises a series of recesses on the lead screw and a plurality of arms extending from an interior of the housing, each arm of said plurality of arms comprising an engagement tab configured to engage a corresponding recess in the series of recesses.

2. The expandable spinal implant of claim 1, wherein the central body comprises a lead screw aperture configured to threadably engage the lead screw, and a wedge positioned adjacent to the lead screw aperture.

3. The expandable spinal implant of claim 2, wherein central body is laterally translatable with respect to the housing.

4. The expandable spinal implant of claim 3, wherein each moveable endplate of the plurality of moveable endplates comprises a ramp on a tapered first end wall, configured to oppose the wedge of the central body.

5. The expandable spinal implant of claim 1, wherein the plurality of moveable endplates comprises an upper moveable endplate and a lower moveable endplate.

6. The expandable spinal implant of claim 5, wherein the upper moveable endplate and lower moveable endplate are each pivotally connected to the housing via one or more pins.

7. The expandable spinal implant of claim 5, wherein the housing comprises a recessed deck configured to receive the upper moveable endplate and the lower moveable endplate in a collapsed configuration.

8. The expandable spinal implant of claim 7, wherein the housing further comprises:
   a first end wall opposite a second end wall;
   a first lateral wall opposite a second lateral wall, wherein the first and second lateral walls extend between the first and second end walls,
   wherein the recessed deck extends along a portion of the first lateral wall, a portion of the second lateral wall, and a portion of the first end wall;
   a ramp disposed on the first end wall; and
   a lip disposed on the first end wall between the ramp and the recessed deck,
   wherein the ramp and the lip are configured to aid in the insertion of the expandable spinal implant into a disc space of a patient.

9. The expandable spinal implant of claim 1, wherein each of the plurality of moveable endplates comprises anti-migration features configured to prevent shifting and to encourage bone growth.

10. The expandable spinal implant of claim 1, wherein the central body comprises a lead screw aperture having an internal thread complimentary to an external thread of the lead screw.

11. The expandable spinal implant of claim 1, wherein the central body comprises one or more anterior supports configured to minimize an amount of motion of the expandable spinal implant relative to an adjacent vertebral body of a patient.

12. The expandable spinal implant of claim 1, wherein the plurality of moveable endplates are configured to pivot relative to the housing, thereby adjusting an angle of lordosis.

13. The expandable spinal implant of claim 12, wherein the angle of lordosis is in a range between one and forty degrees.

14. The expandable spinal implant of claim 1, wherein the lead screw comprises a socket configured to engage an insertion tool.

15. A system comprising:
an expandable spinal implant, comprising:
a plurality of moveable endplates pivotably connected to a housing,
a central body located within the housing,
a lead screw engaged with the central body, and
a passive locking mechanism,
wherein the passive locking mechanism comprises a series of recesses on the lead screw and a plurality of arms extending from an interior of the housing, each arm of said plurality of arms comprising an engagement tab configured to engage a corresponding recess in the series of recesses; and
an insertion tool configured to position the expandable spinal implant into a disc space of a patient.

16. The system of claim 15, wherein the central body comprises a lead screw aperture configured to threadably engage the lead screw, and a wedge positioned adjacent to the lead screw aperture.

17. The system of claim 16, wherein central body is laterally translatable with respect to the housing.

18. The system of claim 17, wherein each moveable endplate of the plurality of moveable endplates comprises a ramp on a tapered first end wall, configured to oppose the wedge of the central body.

19. The system of claim 15, wherein the plurality of moveable endplates comprises an upper moveable endplate and a lower moveable endplate, each endplate pivotally connected to the housing via one or more pins.

20. The system of claim 19, wherein the housing comprises:
a first end wall opposite a second end wall;
a first lateral wall opposite a second lateral wall, wherein the first and second lateral walls extend between the first and second end walls;
a recessed deck configured to receive the upper moveable endplate and the lower moveable endplate in a collapsed configuration,
wherein the recessed deck extends along a portion of the first lateral wall, a portion of the second lateral wall, and a portion of the first end wall;
a ramp disposed on the first end wall; and
a lip disposed on the first end wall between the ramp and the recessed deck,
wherein the ramp and the lip are configured to aid in the insertion of the expandable spinal implant into the disc space of the patient.

* * * * *